(12) United States Patent
Sharpless et al.

(10) Patent No.: US 6,509,506 B1
(45) Date of Patent: Jan. 21, 2003

(54) TWO STEP SYNTHESIS OF D- AND L-α-AMINO ACIDS AND D- AND L-α-AMINO ALDEHYDES

(75) Inventors: K. Barry Sharpless, La Jolla, CA (US); Guigen Li, Lubbock, TX (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/171,538

(22) PCT Filed: May 21, 1997

(86) PCT No.: PCT/US97/08683

§ 371 (c)(1),
(2), (4) Date: Apr. 5, 1999

(87) PCT Pub. No.: WO97/44312

PCT Pub. Date: Nov. 27, 1997

(51) Int. Cl.[7] .................. C07C 205/00; C07C 303/00; C07C 233/00
(52) U.S. Cl. .................. 568/423; 568/424; 564/80; 564/123
(58) Field of Search .................. 562/433; 568/420, 568/423, 424; 564/80, 123, 305

(56) References Cited

U.S. PATENT DOCUMENTS

| | | | |
|---|---|---|---|
| 4,397,786 A | | 8/1983 | Evans, et al. |
| 4,871,855 A | * | 10/1989 | Marko et al. ............ 546/134 |
| 4,990,669 A | | 2/1991 | Reetz et al. |
| 5,200,526 A | | 4/1993 | Arnold et al. |
| 5,322,963 A | | 6/1994 | Shibata et al. |
| 5,346,907 A | | 9/1994 | Kerwin, Jr. et al. |
| 5,399,763 A | | 3/1995 | Satoh et al. |
| 5,545,658 A | | 8/1996 | Alig et al. |

OTHER PUBLICATIONS

Campestrini et al., "Chemoselective Alcohol Oxidations by the Anionic Molybdenum–Picolinate N–Oxidoperoxo Complex", J. Org. Chem. 55: 3658–60 (1990).*
Sharpless, et al., "Osmium–Catalyzed Vicinal Oxyamination of Olefins by Chloramine–T", J. Org. Chem. 41: 177–179 (1976).
Herranz, et al., "Osmium–Catalyzed Vicinal Oxamination of Olefins by N–Chloro–N–argentocarbamates", J. Am. Chem. Soc. 100: 3596–3598 (1978).
Herranz, et al., "Improvements in the Osmium–Catalyzed Oxyamination of Olefins by Chloramine–T", J. Org. Chem. 43: 2544–2548 (1978).
Patrick, et al., "Stereospecific Vicinal Oxyamination of Olefins by Alkylimidoosmium Compounds", J. Org. Chem. 43: 2628–2638 (1978).

Hentges, et al., "Improved Procedure for the Oxyamination of Olefins with Trioxo(tert–butylimido)osmium(VIII)", J. Org. Chem. 45: 2257–2259 (1980).
Herranz, et al., "Osmium–Catalyzed Vicinal Oxyamination of Olefins by N–Chloro–N–metallocarbamates", J. Org. Chem. 45: 2710–2713 (1980).
Bäckvall, et al., "Steroespecific Palladium–Promoted Oxyamination of Alkenes", J. Org. Chem. 45: 2893–2898 (1980).
Martinez, et al., "Highly Enantioselective Ring Opening of Epoxides Catalyzed by (salen)Cr(III) Complexes", J. Am. Chem. Soc. 117: 5897–5898 (1995).
Li, et al., "Catalytic Asymmetric Aminohydroxylation (AA) of Olefins", Angew. Chem. Int. Ed. Engl. 35: 451–454 (1996).
Sharpless, et al., "A New Reaction. Stereospecific Vicinal Oxyamination of Olefins by Alkyl Imido Osmium Compounds", J. Am. Chem. Soc. 97: 2305–2307 (1975).
Jones, et al., "A Convenient Synthesis of Vicinal Diamines", J. Org. Chem. 54: 1940–1943 (1989).
Tamaru, et al., "Palladium(2+)–Catalyzed Intramolecular Aminocarbonylation of 3–Hydroxy–4–pentenylamines and 4–Hydroxy–5–hexenylamines", J. Org. Chem. 53: 5731–5741 (1988).

* cited by examiner

Primary Examiner—Johann Richter
Assistant Examiner—Elvis O. Price
(74) Attorney, Agent, or Firm—Donald G. Lewis; Thomas Fitting

(57) ABSTRACT

D- and L- α-amino acids and D- and L-α-amino aldehydes are synthesized from olefin substrates in two steps. The first step is a catalyzed asymmetric aminohydroxylation addition reaction to the olefin substrate. The addition reaction is catalyzed by osmium and is co-catalyzed by chiral ligands. The chiral ligands, in addition to being co-catalysts with the osmium, also serve to direct the addition reaction regioselectively and enantioselectively, divalent ligands are preferred over monovalent ligands because of their enhanced regio-and enantio-selectivity. As an oxidant nitrogen source for the addition reaction, either a carbamate or sulfonamide may be employed. If carbamate is employed as an oxidant nitrogen source, the resultant β-hydoxycarbamate is deprotected to yield the corresponding β-hydroxyamine. If sulfonamide is employed as an oxidant nitrogen source, the resultant β-hydroxysulfonamide is deprotected to yield the corresponding β-hydroxyamine. The resultant β-hydroxyamine is then selectively oxidized in a second synthetic step to produce the desired D- and L- α-amino acid or D- and L-α-amino aldehyde.

10 Claims, 16 Drawing Sheets

R = CF$_3$-, CH$_3$, -CH$_2$CH$_2$CH$_2$-NH-C(=NH)-NH$_2$, -CH$_2$C(=O)NH$_2$,
-CH$_2$COOH, -CH$_2$SH, -CH$_2$CH$_2$COOH, -CH$_2$CH$_2$CONH$_2$,
-CH$_2$(CH$_3$)CH$_2$CH$_3$, -CH$_2$CH(CH$_3$)$_2$, -CH$_2$CH$_2$CH$_2$CH$_2$-NH$_2$,
-CH$_2$CH$_2$SCH$_3$, -CH$_2$CH$_2$CH$_2$-NH$_2$, -CH$_2$-OH, -CH$_2$(OH)CH$_3$,
-CH(CH$_3$)$_2$,

| Entry | Substrate[a] | Product A[b] | Product B[b] | Yield of A [%][c] | Regioselectivity A:B[d] | ee values [%][e,f] (DHQ)2PHAL A | ee values [%][e,f] (DHQD)2PHAL ent-A |
|---|---|---|---|---|---|---|---|
| 1 | | 23 | B23 | 60 | 66:33 | 93 | −90 |
| 2 | | 24 | B24 | 64 | 66:33 | 93 | −98 |
| 3 | | 25 | B25 | 76 | 88:12 | 97 | −93 |
| 4 | | 26 | B26 | 73 | 80:20 | 98 | −94 |
| 5 | | 27 | B27 | 68 | 88:12 | 91 | −98 |
| 6 | | 28 | B28 | 71 | 75:25 | 90 | −94 |

| Entry | Substrate [a] | Ligand | Solvent | Regioselectivity |
|---|---|---|---|---|
| 1 | BnO-C6H4-CH=CH2 | (DHQ)2PHAL | n-PrOH/H2O | 88:12 |
| 2 | | (DHQ)2PHAL | CH3CN/H2O | 75:25 |
| 3 | | (DHQ)2AQN | n-PrOH/H2O | 33:66 |
| 4 | | (DHQ)2AQN | CH3CN/H2O | 25:75 |
| | | | | |
| 5 | TsO-C6H4-CH=CH2 | (DHQ)2PHAL | n-PrOH/H2O | 50:50 |
| 6 | | (DHQ)2PHAL | CH3CN/H2O | 14:86 |
| 7 | | (DHQ)2AQN | n-PrOH/H2O | 17:83 |
| 8 | | (DHQ)2AQN | CH3CN/H2O | <1:50 |
| | | | | |
| 9 | 3,4,5-tris(BnO)-C6H2-CH=CH2 | (DHQ)2PHAL | n-PrOH/H2O | 88:12 |
| 10 | | (DHQ)2PHAL | CH3CN/H2O | 50:50 |
| 11 | | (DHQ)2AQN | n-PrOH/H2O | 33:66 |
| 12 | | (DHQ)2AQN | CH3CN/H2O | 23:77 |
| | | | | |
| 13 | 3-BnO-4-OMe-C6H3-CH=CH2 | (DHQ)2PHAL | n-PrOH/H2O | 80:20 |
| 14 | | (DHQ)2AQN | n-PrOH/H2O | 33:66 |
| 15 | | (DHQ)2AQN | CH3CN/H2O | 20:80 |

FIG. 13

| Entry | Substrate[a] | Product A[b] | Product B[b] | Yield of A [%][c] | Regioselectivity A:B[d] | ee values [%][e,f] (DHQ)2PHAL A | ee values [%][e,f] (DHQD)2PHAL ent-A |
|---|---|---|---|---|---|---|---|
| 1 | (4-BnO-phenyl vinyl) | 40 | B40 | 68 | 83:17 | 99 | -96 |
| 2 | (3-H3CO-4-BnO-phenyl vinyl) | 41 | B41 | 65 | 75:25 | 99 | -95 |
| 3 | (3-H3CO-5-OCH3-phenyl vinyl) | 42 | B42 | 60 | 75:25 | 97 | -95 |
| 4 | (3-BnO-4-H3CO-phenyl vinyl) | 43 | B43 | 70 | 89:11 | 98 | -96 |
| 5 | (2-naphthyl vinyl) | 44 | B44 | 70 | 88:12 | 98 | -97 |

TWO STEP SYNTHESIS OF D- AND L- α-AMINO ACIDS AND D- AND L- α-AMINO ALDEHYDES

RELATED APPLICATIONS

The present application is a US national phase application and claims priority from International Application Serial No. PCT/US97/08683, filed May 21, 1997, which claimed priority from U.S. application Ser. No. 08/651,228, filed May 22, 1996, which issued as U.S. Pat. No. 5,994,583, on Nov. 30, 1999.

GOVERNMENT RIGHTS

This invention was made with government support under Grant Nos. GM-28384, GM-37696, GM-28485 and AI-15136 awarded by the National Instiutes of Health. The U.S. government has certain rights in the invention.

FIELD OF INVENTION

The invention relates to the synthesis of D- and AL-α-amino acids and D- and L- α-amino aldehydes from olefins and other unsaturated substrates. More particularly, the invention relates to a two step synthesis in which the first step is an asymmetric β-aminohydroxylation of the olefin or unsaturated substrate and the second step is an oxidation of the deprotected product of the first step to form a D- or L- α-amino acid or a D- or L- α-amino aldehyde.

BACKGROUND

D- and L- α-amino acids are key building blocks for peptides, proteins, pharmaceuticals, and other important biomolecules. Naturally occurring L- α-amino acids are readily available from biological sources. However, enantiomerically pure D- α-amino acids and unnatural L- α-amino acids are more difficult to obtain. Due to their chirality, these compounds can be difficult to synthesize in an enantiomerically pure form. Several compounds within this class have significant economic value. Similarly, and D- and L- α-amino aldehydes are a re-occurring motif in biologically and pharmaceutically important molecules but are difficult to obtain in enantiomerically pure form.

Over the past 20 years, separate and distinct synthetic methodologies have been developed by Sharpless et al. for the vicinal hydroxyamination of olefins. There are three major groups of oxyamination procedures which produce aminoalcohols (Sharpless et al. *J. Am. Chem. Soc.* 1975, 97, 2305; Sharpless et al. *J. Org. Chem.* 1978, 43, 2628; Sharpless et al. *J. Org. Chem.* 1980, 45, 2257), hydroxysulfonamides (Sharpless et al. *J. Org. Chem.* 1976, 41, 177; Sharpless et al. *J. Org. Chem.* 1978, 43, 2544; Sharpless et al. *J. Org. Chem.* 1979, 44, 1953; Sharpless et al. *Org. Syn.* 1980, 61, 85) or hydroxycarbamates (Sharpless et al. *J. Am. Chem. Soc.* 1978, 100, 3596; Sharpless et al. *J. Org. Chem.* 1980, 45, 2710; Sharpless et al. U.S. Pat. No. 's 4,871,855; 4,965,364; 5,126,494; EP 0 395 729). Each oxyamination procedure has unique reaction conditions and includes variations in solvents, auxiliary salts, nucleophiles, temperature, stoichiometric v. catalytic amounts of osmium species and stoichiometric v. catalytic amounts of ligand. Each procedure is highly dependant on the nature of the substrate and possesses unique properties which afford different yields, chemoselectivities, stereoselectivities, regioselectivities and enantioselectivitive outcomes.

1. Aminoalcohols

The first reported oxyamination procedure (Sharpless et al. *J. Am. Chem. Soc.* 1975, 97, 2305) generated aminoalcohols from mono and di substituted olefins, using stoichiometric quantities of a tri-oxo(tert-butylimido)osmium species. The procedure required reductive cleavage of the osmate ester which was performed with lithium aluminum hydride and afforded tertiary vicinal aminoalcohols. Yields were good to excellent, but in some cases, the side product vicinal diol was formed as an undesired by-product. The stereochemistry of addition, in methylene chloride or pyridine, was exclusively cis (Sharpless et al. *J. Org. Chem.* 1978, 43, 2628). In addition, the carbon-nitrogen bond formed was, in every case, at the least substituted olefinic carbon atom. Di and tri-substituted olefins reacted much slower with the generated imido reagent than with monosubstituted alkenes; tetrasubstituted alkenes yielded only the corresponding diol. However, by using a coordinating solvent such as pyridine, higher yields and higher ratios of aminoalcohol to diol were reported. Sharpless et al. *J. Org. Chem.* 1980, 45, 2257; Sharpless et al. *J. Org. Chem.* 1976, 41, 177; Sharpless et al. *J. Org. Chem.* 1978, 43, 2544.

2. Hydroxysulfonamides

Sharpless et al. first demonstrated that hydroxysulfonamides could be obtained using either stoichiometric or catalytic amounts of 1% osmium tetraoxide in the presence of 1.5–5 equivalents of Chloramine-T trihydrate ($TsSO_2NClNa.3H_2O$, Ts=tosylate; commercially obtained) to effect cis addition of a hydroxyl (OH) and an arylsulfonamide moiety (Ar—$SO_2NH$) across a mono or disubstituted olefinic linkages (Sharpless et. al. *J. Org. Chemistry* 1976, 41, 177).

Two procedures were developed to effect hydroxyamination of olefins using sulfonamides. (Sharpless et al. *Org. Syn.* 1980, 61, 85). The first procedure used phase transfer catalysis conditions at 55–60° C. With 1% $OsO_4$, 1:1 v/v, 0.20 Molar $CHCl_3/H_2O$, and benzyltriethylammonium chloride as the phase transfer catalyst. The chloramine T-trihydrate ($TsSO_2NClNa.3H_2O$) was either added directly or formed in situ in water; this solution was then directly used in the phase transfer mixture. The in situ procedure, for generating the chloramine salts, involved stirring a suspension of the arylsulfonamide with an equivalent of sodium hypochlorite (Clorox) until a homogenous solution was obtained. The yields were comparable with those obtained with isolated chloramine salts and the procedure was found most effective for monosubstituted and 1,2 disubstituted olefins. The phase transfer method, however, gave poor results with trisubstituted and 1,1-disubstituted olefins and the procedure did not succeed with diethyl fumarate and 2-cyclohexen-1-one. Sharpless et al. *J. Org. Chem.* 1978, 43, 2544.

A second procedure was carried out in tert-butyl alcohol at 55–60° C. with 1% $OsO_4$, silver nitrate (with or without) and commercially obtained chloramine T-trihydrate ($TsSO_2NClNa.3H_2O$) which provided the only source (of water. The procedure did not succeed with tetramethylethylene and cholesterol, and negative results were found with most hindered tri- and tetrasuostituted olefins. Sharpless et. al. *J. Org. Chemistry* 1976, 41, 177; Sharpless et al. *Org. Syn.* 1980, 61, 85. The addition of divalent metal salts such as $AgNO_3$ and $Hg(NO_3)_2$ improved some reactions, however, other reactions suffered deleterious effects from the addition of the metal salts. Sharpless et al. *J. Org Chem.* 1978, 43, 2544; Sharpless et. al. *J. Org. Chemistry* 1976, 41, 177.

Further elaboration on either procedure showed that other sulfonamide derivatives ($ArSO_2NClNa$) could be successfully employed in addition to chloramine T, where Ar=phenyl, o-tolyl, p-chlorophenyl, p-nitrophenyl, and o-carboalkoxyphenyl. Sharpless et al. *J. Org. Chem.*1978, 43, 2546.

Neither the phase transfer catalyst or tert-butyl alcohol procedures succeeded with tetramethyl ethylene, 2,3-dimethyl-2-octene, diethyl fumarate, or 2-cyclohexen-1-one. Negative results were also obtained with most hindered tri- and tetrasubstituted olefins. Herranz E., MIT Ph.D. Thesis, 1979, 33.

Solvent conditions for the synthesis of the hydroxysulfonamides included organic solvents such as acetonitrile, tert-butyl alcohol, isopropyl alcohol and chloroform which was in contact with the aqueous phase in the phase transfer catalyst procedure.

The tert-butyl alcohol procedure (including other solvents used) was not run with added water; the phase transfer catalyst (PTC) procedure required a biphasic mixture of 1:1 v/v chloroform/water. Recently, however, an improvement was reported which used a 1:1 ratio of organic solvent to water in a homogeneous, rather than a biphasic solution or organic solvent with small amounts of water. These conditions were found to provide optimum enantioselectivity, regioselectivity and improved yields from either the previously described t-butyl alcohol or PTC conditions. Sharpless et al. *Angew. Chemie Intl Ed.* 1996, 35, 451.

The use of chiral ligands with sulfonamides provides enantioselectivity and has been observed to both accelerate and decelerate the rate of catalysis. The hydroxysulfonamide process is a stereoselective cis process. The presence of ligands also has a dramatic effect on the regioselectivity. In a study with no ligand present with methyl cinnamate, the two regioisomers were present in a 2:1 ratio. With the addition of ligand, the ratio was improved to 5:1 or greater. Another positive effect of the ligand was its ability to suppress formation of diol by-product. *Agew. Chemie Intl Ed.* 1996, 35, 451.

Peferred ligands for use with sulfonamides have included the use of monovalent cinchona alkaloids or the bivalent phthalazine based, commercially available $(DHQ)_2PHAL$ and $(DHQD)_2PHAL$ alkaloids. Sharpless et al. *Angew. Chemie Intl Ed.* 1996, 35, 451.

Temperature conditions for the hydroxysulfonamide asymmetric aminohydroxylations have varied from 60° C. to 25° C. for reactions including sulfonamides, auxiliary salts, ligands, phase transfer catalysts and stoichiometric or catalytic osmium species, primarily in organic solvents with small amounts of water. Recently, it has been shown that temperature can be lowered to 0° C. while running the reaction, to obtain product by filtration; many hydroxysulfonamides tend to be highly crystalline Sharpless et al. *Acta Chemica Scandinavica* 1996 in press.

Cleavage of the sulfonamides, to free aminoalcohols, have accomplished via standard deprotection conditions including dissolving metals (Na, $NH_3$; Sharpless et al *J. Org. Chem* 1976, 41, 177) and HBr, acetic acid and phenol (Fukuyama et al. Tetrahedron Lett. in press)

3. Hydroxycarbamates

A drawback with the hydroxysulfonamide procedure was that cleavage conditions were too strong for some substrates. The use of carbamates to protect the nitrogen, however, provided a methodology which avoided the use of harsh acids or reducing deprotection problems found with hydroxysulfonamides (Sharpless et al. *J. Am. Chem. Soc.* 1978, 100, 3596; Sharpless et al. *J. Org. Chem.* 1980, 45, 2710; Sharpless et al. *Org. Syn.* 1981, 61, 93; Sharpless et al. U.S. Pat. No. 's 4,871,855; 4,965,364; 5,126,494; EP 0 395 729).

Sharpless first demonstrated the synthesis of hydroxycarbamates with the use of N-chloro-N-argentocarbamates (Sharpless et al *J. Am. Chem. Soc.* 1978 100, 3596). The N-chloro-N-argentocarbamates were generated in situ via the addition of N-chlorosodiocarbamates and silver nitrate to a solution of the olefin in acetonitrile or tert-butanol with trace amounts of water (4.5 molar equivalents based on olefin) and 1% of osmium tetroxide catalyst to generate vicinal hydroxycarbamates in generally good yields. The methodology was reported to be more effective with electron deficient olefins such as dimethyl fumarate and trisubstituted olefins were reported to be less readily oxyaminated with N-chloro-N-argentocarbamates than with the chloramine-T procedures (Sharpless et. al. *J. Org. Chem.* 1976, 41, 177).

Sodio-N-chlorocarbamates were always first converted to either argento or mercurio salt analogs. The addition of the $AgNO_3$ or $Hg(NO_3)_2$ salts, to make N-chloro-N-argentocarbamates or mercuric salt analogs, was crucial for the reaction to retain its desired properties. (Sharpless et al *J. Org. Chem.*, 1980, 45, 2711). This was in contrast to the sulfonamide conditions, where the sodio-N-chlorosulfonamide salts could be used directly with either the ti-butanol or chloroform/water—phase transfer catalyst procedures (Sharpness et al. *J. Org. Chem.* 1978, 43, 2544).

The addition of nucleophiles such as tetraethylammonium acetate were also proven to be beneficial to the reaction in the procedures using the silver and mercury salts of the chloramines from carbonates. Alternatively, the reactivity and yields were enhanced by addition of excess $AgNO_3$ and $Hg(NO_3)_2$ (over that needed to react with the NaClNCOOR salt) Sharpless et al. *J. Org Chem.* 1980, 45, 2710.

Preferred conditions included employment of $ROCONClNa+Hg(NO_3)_2+Et_4NOAc$ with N-chloro-N-sodiocarbamates; these conditions were recommended as the best procedure for mono, di and tri substituted olefins even including some olefins unreactive in all of the various chloramine T based processes. (Sharpless et al. *Org. Syn.* 1981, 61, 93).

Among the carbamates tried, it was found that both benzyl N-chloro-N-argentocarbamate and tert-butyl N-chloro-N-argentocarbamates (or mercurio analogs) were among the most effective oxidants, especially with addition of nucleophiles such as tetraethylammonium acetates Other carbamates such as isopropyl, ethyl, menthyl and bornyl derivatives were also used, however, chemo, regio and stereoselectivities were lower. Virtualy no asymmetric induction was observed when chiral menthyl or bornyl derived carbamates were employed for hydroxyaminations. (Sharpless et al *J. Am. Chem. Soc.* 1978 100, 3596).

Sharpless disclosed the use of stoiciometric amounts of a first generation monovalent alkaloid ligand with a tert-butyl derived N-chloro-N-argent(carbamate for hydroxyamination in a series of patent applications directed to ligand accelerated catalytic asymmetric dihydroxylation. These disclosures illustrated an hydroxyamination on trans-stilbene with the use of 1.0 equivalent (stoichiometric to olefin) of monovalent DHQD-p-chlorobenzoate (DHQD=hydroquinidine) ligand, 1 mol % osmium tetroxide, silver nitrate (figure) or mercuric chloride (0.80 equivalents; in protocal), 0.09 Molar acetonitrile (93.11 volume % acetonitrile)/water mix (6.89 volume % water) and tertbutyl derived N-chloro-N-argeniocarbamate (1.45 equivalents) at 20° C. (figure) or 60° C. (protocal) for 1 hour. The disclosure reported a 51% ee with a 93% yield of aminoalcohol. (Sharpless et al. U.S. Pat. No. 's 4,871,855; 4,965,364; 5,126,494; EP 0 395 729).

In a review on ligand accelerated catalysis, Sharpless et al. noted that a 92% ee had been achieved in a stoichiometric reaction of trioxo-(tert-butylimido) osmium with stilbene in the presence of DHQD-CLB at ambient temperatures (Sharpless et al. *Angew. Chem. Int. Ed. Engl.* 1995, 34, 1059, ref. 80 "unpublished results"); this mention did not disclose reaction conditions.

Recently, an oxyamination reaction for the hemisynhesis of taxol and analogs was reported using a tertbutyl derived N-chloro-N-argentocarbamate, excess silver nitrate or other metallic salts, with the use of either catalytic or stoichiometric amounts of osmium and the addition of stoichiometric amounts of monovalent DHQD (hydroquinidine), DHQ (hydroquinine) ligands in an unsuccessful attempt to influence the diastereoselectivity and the regioselectivity of the aminohydroxylation process. Solvent conditions varied from acetonitrile, toluene or pyridine, and the reactions were carried out at 4° C. to room temperature, in the dark. The study reported that quinuclidine ligand. had no effect on the amino alcohol yields but found that the addition of chiral tertiary amines had some beneficial effect on the yields of the various amino alcohol isomers formed. (Mangatal et al. *Tetrahedron* 1989 45, 4177). However, the two pseudoenantiomeric alkaloid ligands (i.e. DHQ-OAc and DHQD-OAc; OAc=acetate) gave a mixture of stereo and regionsomeric products. The result indicates that this particular hydroxyamination process (be it stoichiometric or catalytic was unclear) had exhibited no "asymmetric" effects. The procedure can therefore not be regarded as an asymmetric aminohydroxylation.

As a whole, the prior art uses hydroxycarbamates which always run at room temperature with either argento or mercurio salt analogs, monovalent ligands, stoichiometric or catalytic osmium species and organic solvents with trace amounts of water. (Sharpless et al. *J. Am. Chem. Soc.* 1978, 100, 3596; Sharpless et al. *J. Org. Chem.* 1980, 45, 2710; Sharpless et al. U.S. Pat. No. 's 4,871,855; 4,965,364; 5,126,494; EP 0 395 729).

Cleavages of the hydroxycarbamates, to free aminoalcohols, are well known in the art and include mild acid or base hydrolysis and catalytic hydrogenolysis, depending on the attached functionality to the carbamate. (Greene, *Protective Groups in Organic Synthesis*, 1981, Wiley, 1st edn. pp. 223–249).

What is needed is an improved method for synthesizing D- and L- α-amino acids and D- and L- α-amino aldehydes using olefins as starting materials.

SUMMARY OF THE INVENTION

One aspect of the invention is directed to methods for the conversion of olefinic substrates to form asymmetric α-amino acid products. The method employs two steps.

In the first step the olefinic substrate is catalytically converted by means of an addition reaction to form a protected asymmetric β-aminohydroxide product having a protected amino radical and a hydroxyl radical. The conversion employs a reaction solution which includes a source of the protected amino radical, osmium as a catalyst, a chiral ligand or enantiomerically directing the asymmetric addition, and a solvent.

There are several modes for accomplishing this first step. In a first preferred mode, the source of the protected amino radical is a carbamate. In a second preferred mode, the source of the protected amino radical is a sulfonamide. In the first preferred mode, the chiral ligand may be present and soluble within the reaction solution at a concentration within a range approximately excellent to the catalytic concentration of the osmium. The solvent may have an organic component within which the olefinic substrate and carbamate are present and soluble at stoichiometric concentrations and within which the osmium is present and soluble in catalytic concentrations. The solvent may also include an aqueous component present at 10% or greater on a volume basis. Alternatively, the chiral ligand may be present and soluble within the reaction solution at a molar concentration which is approximately equivalent to the catalytic concentration of the osmium but which is less than the stoichiometric concentration of the olefinic substrate and carbamate.

In the second step, the hydroxyl radical on the asymmetric β-aminohydroxide product of the first step is oxidized to form the asymmetric α-amino acid product. The protected amino radical may be deprotected either prior to or after the oxidation of the hydroxyl radical.

Another aspect of the invention is directed to methods for the conversion of olefinic substrates to form asymmetric α-amino aldehyde products. This second aspect of the invention employs two steps, viz.

1. An addition reaction wherein the olefinic substrate is converted to the protected asymmetric β-aminohydroxide product described above; and
2. An oxidation step where the product of the first step is converted to an asymmetric α-amino aldehyde product.

The protected amino radical may be deprotected either before or after the oxidation step. In a preferred mode, the deprotection is perform simultaneously with the oxidation step.

DESCRIPTION OF FIGURES

FIG. 13 shows a table which illustrates the influence of ligand and solvent on regioselectivity in the AA reaction of four styrene derivatives wherein [a] All reactions were performed on 1.0 mmol scale using 4% K2OsO2(OH)4 5%, ligand and the solvent given in the table at 25° C. for 1 h. [b] Ratio of benzylic amine A/benzylic alcohol B regioisomers determined by 1H NMR.

FIG. 14 shows a table which illustrates the AA reaction using t-BuOC(O)NNaCl as the nitrogen source wherein [a] All reactions were performed on 1.0 mmol scale using 4% K2OsO2(OH)4 6% ligand and n-PrOH/water (2:1) at 0° C. for 1 h. [b] Major regioisomer using (DHQ)2PHAL. [c] Isolated yield of regioisomer A using (DHQ)2PHAL. [d] Ratio of benzylic amine A/benzylic alcohol B regioisomers detemined by 1H-NMR. [e] The BOC groups were replaces by Cbz groups and ee-values were determined by chiral HPLC (chiralcel AD column). [f] The "negative" ee values are meant to emphasize that with (DHQD)2PHAL as ligand the mirror image isomer dominates (i.e. A>ent-A).

DETAILED DESCRIPTION

An interesting class of α-amino acids are the aryl glycines which are found in a wide range of bioactive compounds such as amoxicillins, nocardicins, cephalecins and glycopeptide antibiotics (e.g. vancomycin). Besides the naturally occurring aryl glycines, there are also a number of important synthetic aryl glycines, for example, those appearing as side chain moieties in semi-synthetic penicillins and cephalosphorins. Despite the simple molecular structure of these compounds, their nonracemic syntheses have been plagued by the ease of base-catalyzed epimerization involving the α-methine proton in synthetic intermediates. Several research groups have achived syntheses of this class of amino acids, but these routes generally suffer from poor optical and/or chemical yields.

Figure 9:
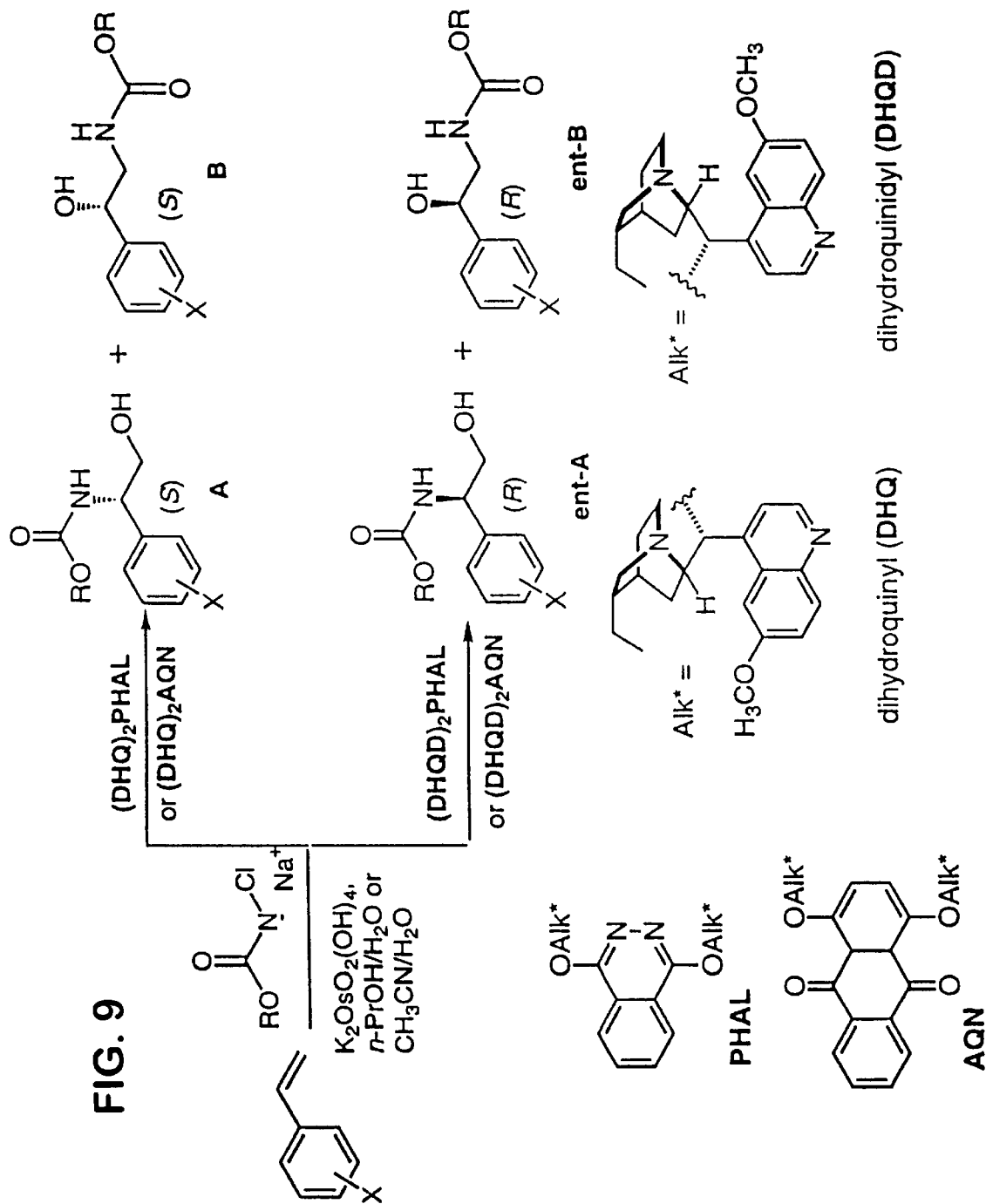
FIG. 9 illustrates the AA reactions of substituted styrenes (X=alkyl, halogen, phenyl, OR', $NO_2$, $CF_3$, CN) using carbamates (R=benzyl, t-butyl). DHQD-H= dihydroquinidine, DHQ-H=dihydroquinine, PHAL=1,3-phthalazinediyl.

We have found that the catalytic asymmetric aminohydroxylation (AA) reaction directly effects the synthesis of either the (R)- or (S)-α-aryl-Cbz or Boc-protected amino alcohols from commercially available styrenes (FIG. 9). The enantioselectivities are excellent and the yields are generally good. Subsequent oxidation of the primary alcohol functionality yields the coresponding α-aryl glycines.

The osmium-catalyzed asymmetric amino hydroxylation (AA) reaction first emerged as a process in which the nitrogen source was chloramine salts of sulfonamides. These original sulfonamide-based AA procedures, although efficient, lacked substrate scope. For example, styrenes were conspicuously absent from the list of olefins which succeed in these systems. The replacement of sulfonamides by alkyl carbamates or by amides has greatly improved the AA in both scope and selectivity. Styrenes, very poor substrates under the sulfonamide-based AA conditions, became excellent substrates under the carbamate-based conditions. In fact, as in the catalytic asymmetric dihydroxylation (AD), styrenes are among the best substrates for this new carbamate—based AA process, and they also obey the same face selection rule established for the AD reaction. Additionally, all styrene derivatives studied to date exhibit the desirable phenomenon of ligand-accelerated catalysis (LAC). We report here carbamate AA reactions on a wide range of substituted styrenes. Enantinselectivities of up to 99% and yields of up to 80% for the major regioisomer (typically the one with the benzylic-NHR) make styrenes excellent substrates for the new carbamate-based AA reaction.

Figure 10:
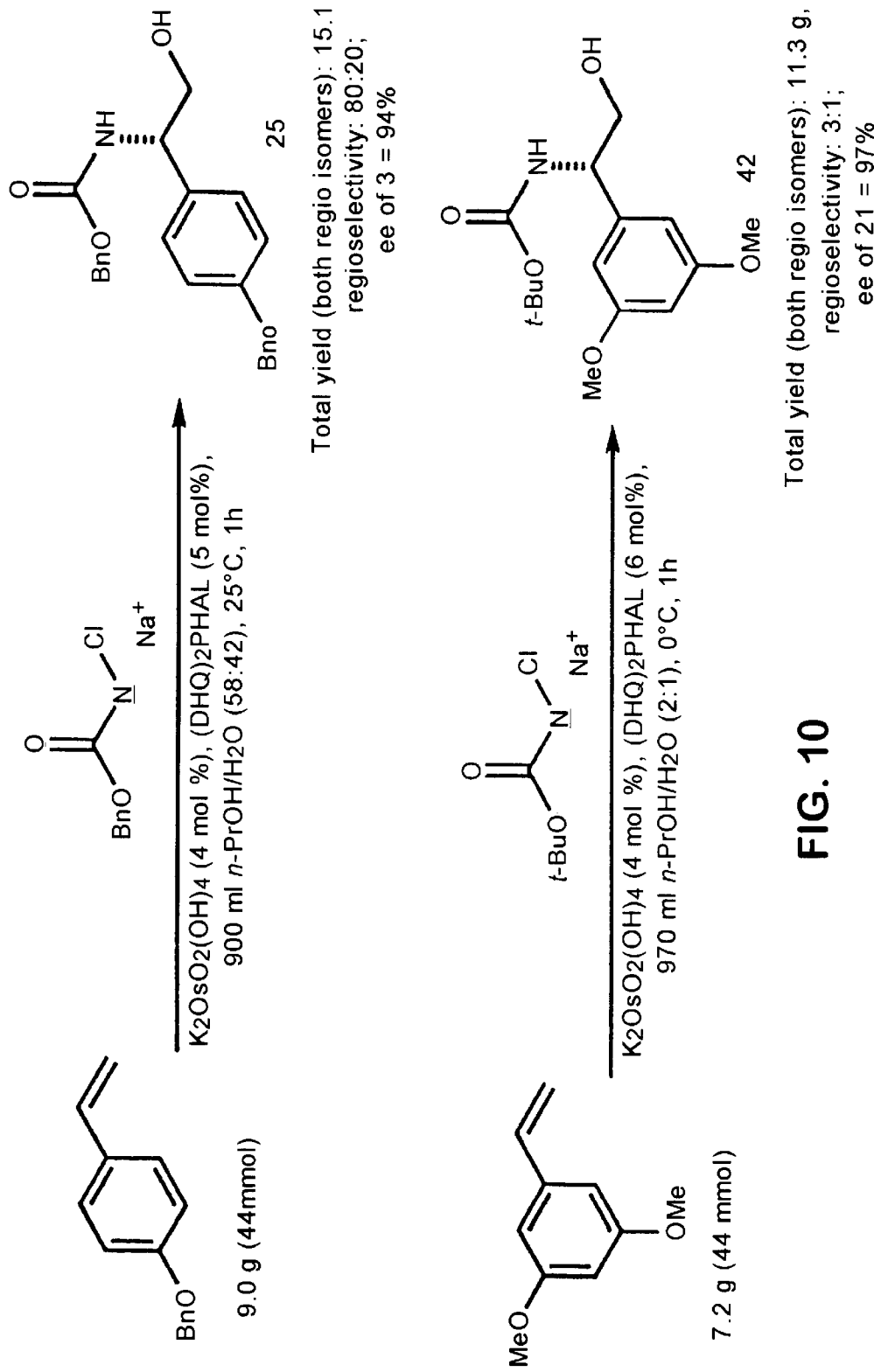
FIG. 10 exemplifies the AA reaction on styrene derivatives using carbamates.

Effective experimental conditions for styrenes in the AA process using benzyl carbamates employ 4 mol % K2OsO2 (OH)4, 5 mol % alkaloid ligand (DHQ)2PHAL or (DHQD) 2PHAL, 3.1 eq. BnOC(O)NNaCl and n-PrOH/H2O (1:1) at 25° C. The results are summarized in the table shown in FIG. 12, which although largely self explanatory, are deserving of a few comments. The regioselectivity is seen to be highly dependent on the nature of the styrene as well as the choice of ligand, solvent and ligand-solvent combination (FIG. 10). Phthalazne ligands such as (DHQ)2PHAL or (DHQD) 2PHAL in n-PrOH (alcoholic solvents) favor the benzylic amine (A) over the benzylic alcohol regioisomer (B) (all entries in FIG. 12 and entries 1, 9 and 13 in FIG. 14), but in acetonitrile, the ratio of benzylic amine to benzylic alcohol (A/B) decreases significantly (entries 2 and 10 in FIG. 14) and in one case actually reverses (entry 6, FIG. 14). The recently introduced anthraquinone (AQN) ligands appear to strongly favor this reversal of regioselectivity, and when used in conjunction with the CH3CN/H2O solvent system the ratio of B/A reaches its zenith (entries 4, 8, 12 and 15 in FIG. 14). AA reaction using BnOC(O)NNaCl as the nitrogen source.

Hence, the AA protocol now enables the selective synthesis of either regioisomeric amino alcohol. The absolute stereo chemistry of several of these amino alcohol was determined by comparison with authentic samples of regioisomers of both types A and B. For the substrates studied the enantiofacial selectivity of the AA reaction is soley determined by the ligand (DHQ type vs DHQD, type) and is not dependent on the regioisomer formed. The configurations of the other entries in the tables are provesonally assigned by assuming that the same face-selection rule is also operative for the other substrates.

The phenylglycinols A are favored using the phthalazine-based ligand-n-PrOH solvent combination and the 2-amino-1-phenyl ethanols B, important adrenergic drugs, are obtained using the anthraquinone-based ligand-CH3CN solvent combination. In fact, if the latter outcome is desired than even greater selectivity for isomer B is available using the recently reported amide-version of the AA. The amide-AA has the possible disadvantage of a less easily removed nitrogen protecting group, on the other hand, it needs only a slight excess of the chloramine salt compared to the present carbamate-version of the AA.

Initially, the tert-butyl carbamate-based AA reactions were carried out in the same way as the benzyl carbamate-based reactions, but the results were disappointing. Poor chemoselectivity (i.e., substantial diol formation) and low yields were observed (entries 1, 2 and 3, FIG. 13). Solvent variation (e.g. EtOH or t-BuOH instead of n-PrOH) gave no improvement. In CH3CN/H2O (1:1), formation of diol was suppressed, however, at the expense of regioselectivity. We were assuming that higher water content could only be advantageous, because it should accelerate the hydrolysis in the catalytic cycle and thereby suppress the involvement of the rate and selectivity damaging second cycle. But we soon realized that the higher water concentrations, at least in this particular case (i.e. styrenes and t-alkyl-carbamate based chloramines) also leads to competing hydrolysis of the putative ROCON=OsO3 complex, affording OsO4 which of course leads to dihydroxylation. This side reaction is suppressed when the percentage of solvent water is reduce. The best results were obtained with 4 mol % of K2OsO2(OH)4, 6 mol % of ligand at 0° C. and a 2:1 ratio of n-PrOH/water as the solvent. Under these conditions good regioselectivities and excellent enantioselectivities were realized (FIG. 13). Compared to the benzyl carbamate series, the t-butyl carbamate series still affords slightly poorer regioselectivities and yields, but the enantioselectivities approach 100% in each case. Both the Z- and BOC-AA reactions are fast, independent of the substituents present on the styrene. We assume that in the case of styrenes the catalytic process is dominated by turnover in the "first cycle".

Preparative scale (44 mmol) applications of the standard (benzyl carbamate) and the "modified" (t-butyl carbamate) procedures are given in FIG. 10 for 4-benzyloxy styrene and 3,5-dimethoxy styrene, respectively. In these two cases, working on large scale greatly simplified isolation and purification of the AA product. In the benzyl carbamate case, the workup simply involved diluting the reaction mixture with walter to precipitate the product 25 (regioisomer ratio 80:20)$_R$, isolation of the resulting solid by filtration, and, finally, triturating it with cold n-PrOH. In the t-butyl carbamate case, precipitation of the product was induced by concentration of the reaction mixture to ca. one third its volume on a rotary evaporator. Filtration of the resulting slurry gave the product 42 (regiosiomer ratio 66:33) (FIG. 10). Thus, in both cases the usual extractive workup, even the initial quenching with sodium sulfite is omitted. Perhaps the most important advantage of these large scale procedures is that all the excess carbamate (or its N-chloro salt) remain in the filtrate.

Figure 11:
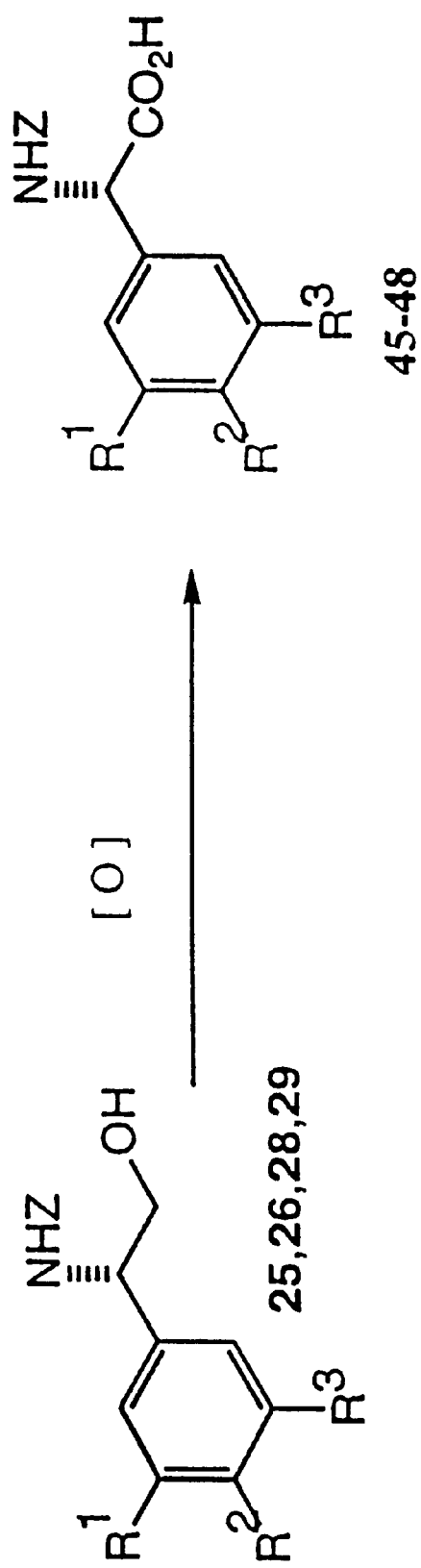
FIG. 11 illustrates oxidation of the α-aryl glycinols to the corresponding α-aryl glycines wherein 25→25: R1=R3=H, R2=OBn 75%; 26→26: R1=R3=OMe, R2=H; 73%; 28→27: R1=OMe, R2=OBn, R3=H; 71%; 29→48: R1=R2=R3=OMe; 75%.

The second step requires oxidation of the protected amino alcohols to the corresponding amino acids. The direct oxidation of the primary alcohol to the desired carboxylic acid was accomplished via the ruthenium-catalyzed periodic acid oxidation, but in some cases poor yields were obtained. TEMPO catalyzed NaOCl oxidation proved generally more effective (FIG. 11). The oxidation step works equally well on the crude mixture of the two regioisomers yielding a carboxylic acid or a ketone, respectively. The acid can be easily separated from the ketone due to its higher polarity. In most of the cases, 70–80% yields were obtained and no epimerization was detected.

In the optimization of this reaction it was found that 1.05 eq. of TEMPO was necessary to obtain the desired oxidation product. When a catalytic amount of TEMPO was employed, a chlorinated aromatic derivative was isolated as the major product (presumably the TEMPO scavenges any chlorine which is liberated during the reaction provided ca. 1 eq. is present). In these (FIG. 11) and several other cases23 examined to date, the configurational integrity of the stereogenic center is maintained during the oxidation. However, it remains to be seen if the stereocenter survives in the strongly electron-deficient cases (e.g. entries 11–15, FIG. 12). in these latter cases, the slightly acidic catalytic RuO4/H5IO6 oxidation process might be better than TEMPO/NaOCl method.

In conclusion, the catalytic aminohydroxylation reaction provides access to both enantiomers of N-carbamate protected α-aryl glycines with excellent enantioselectivities and in high yields. This two-step-procedure appears to be one of the most efficient and flexible routes to this class of amino acids in enantiomerically pure form.

Synthetic Protocols

General Experimental

All reagents and solvents were purchased from commercial sources and used as received unless seated otherwise. All commercial chemicals were used without purification and their stoichiometries were calculated based on the reported purities from the manufacturer. (DHQD)$_2$PHAL, 95% (hydroquinidine 1,4-phthalazinediyl diether)., (DHQ)$_2$PHAL, 97% (hydroquinine 1,4-phthalazinediyl diether), chloramine-T-hydrate 98% (N-chloro-p-toluenesulfonamide, sodium salt) are commercially available from Aldrich Chemical Company. Additionally, the (DHQ)$_2$ and (DHQD)$_2$ ligands can be prepared from the procedure of Sharpless et al. *J. Org. Chem.* 1992, 57, 2768. Melting points were measured without correction with a Thomas-Hoover capillary apparatus. Optical rotations were recorded on an Autopol III polarimeter (Rudolph Research, Fairfield, N.J.) $^1$H and $^{13}$C NMR spectra were recorded on a Bruker AMX 400 instrument. Stoichiometries are calculated based on the purities reported by the manufacturer (trans-stilbene: 96%; Chloramine-T trihydrate: 98%). The K$_2$OsO$_2$(OH)$_4$ should be mauve rather than brown/black and should be dry for the best yields and ee's (the hygroscopic nature of the salt affects the amount of osmium dispensed). All new compounds gave satisfactory spectroscopic analyses ($^1$H-NMR, IR, HRMS). Enantiomeric excesses (ee's) were determined by HPLC using Chiracel columns (Daicel Chemical Industries) and isopropanol/hexane (v/v) mobile phases; the retention time of the major enantiomer from the (DHQ)$_2$-PHAL reaction is in italics. The vicinal hydroxysulfonamides derived from AA reactions using (DHQ)$_2$-PHAL as the chiral ligand were correlated to compounds of known absolute configuration by HPLC.

Oxidation Conditions to Aminoacids from Hydroxycarbamates or Hydroxysulfonamides Procedure as adapted from Sharpless et al *J. Org. Chem.* 3937 (46), 1981. A convenient vial or flask is charged with a magnetic stirring bar, 2 mL of carbon tetraclloride, 2 mL of acetonitrile, 3 mL of water, 1 mmol of β-sulfonamide alcohol or β-carbamate alcohol substrate, and 4.1 mmol of (4.1 equiv.) of periodic acid, and 5 mg (2.2 mol %) of ruthenium trichloride hydrate (all reagents commercially available from Aldrich). The reaction mixture is stirred at room temperature for 0.5 to 1 h. Then 10 mL of ethylacetate (EtOAc) is added and the phases are separated. The aqeous phase is extracted 3 times with EtOAc. The combined organic phases are then dried (MgSO4), filtered through Celite pad. 0.90 mmol of NMR sure product was obtained after concentration and vacuum drying. The acid is then transferred its methyl ester and reduced back to (S) N-benzyl phenylglycinol. Chirality is maintained.

Other oxidation conditions include, but are not limited to: $KMnO_4$/NaOH: Garner et al., Tetrahedron Lett., 5855–58, 1984; $RuO_2$: Martin, Tetrahedron Lett., 2701–02, 1988. $K_2CrO7/H_2SO_4$: J. Am Chem. Soc., 2498, 1960; $PtO2$: *J. Org. Chem.* 4898, 1987.

Oxidation Conditions to Aminoaldehydes from Hydroxycarbamates or Hydroxysulfonamides Procedure adaptoed from Russo, et al *J. Org. Chem.* 3589 (58), 1993. A solution of β-sulfonamide alcohol or β-carbamate alcohol substrate (10.7 mmol) in 15 mL of $CH2Cl2$ was cooled to 0° C. The rapidly stirring solution was treated with 6.9 mL in $CH2Cl2$ of TEMPO (Aldrich), 1.5 mL of 0.75 M KBr, and 0.22 g of Aliquat 336. Aqeous NaOCl (0.4 M, 67 mL) was brought to pH 9 with $NaHCO3$ and added dropwise . After the addition of the aqeous NaOCl solution, the biphasic reaction was stirred for an additional 10 min. at room temperature. The pH of the mixture was adjusted to 12 with NaOH when the reaction was complete.

Other oxidation conditions include, but are not limited to oxidations well known in the art, including Swern, $SO_3$/pyridine or PCC oxidations, to achieve the aldehyde.

Chloramine Sodium Salt Preparation

Procedure as adapted from Campbell et al. *Chem. Rev.*, 1978, 78, 65.

General Asymmetric Aminohydroxylation Conditions With Carbamates:

To a solution of NaOH (3.05 equivalents) in 0.13 Molar equivalent of water to olefin is added desired carbamate (3.10 equivalents). The resulting solution is stirred at room temperature for 10 min and then t-butyl hypochlorite (3.05 equivalents; Aldrich Chemical) is added dropwise. The above solution is stirred for another 10 min and then 0.13 Molar equivalent of n-propanol (t-butanol or acetonitrile can be substituted) and $(DHQ)_2$-PHAL (0.05 equivalents, 5 mol %; $DHQD_2$-PHAL obtains antipode) are added to form a homogeneous solution. The reaction mixture is immersed in a room temperature bath and added substrate olefin (1 equivalents) and $K_2OsO_2(OH)_4$ (0.04 equivalents, 4 mol %) are then added. The reaction is stirred for 45 min with the color changing from light green to light yellow, followed by quenching by addition of aqueous sodium sulfite; the phases are separated, and the aqueous phase was extracted with ethyl acetate. The combined organic extracts are washed with water and brine, dried over $MgSO_4$ and the solvent concentrated to give the crude product. Flash chromatography of this material provides the hydroxycarbamate product.

Solvent Variations:

Preferred solvents include acetonitrile, n-propanol, tert-butanol.

Suitable solvents include methanol, ethanol, n-butanol, n-pentanol, 2-Propanol, 2-Butanol, tert-butanol, ethylene glycol; nitriles: acetonitrile, propionitrile; ethers: tetrahydrofurane, diethyl ether, tert. butyl methyl ether, dimethoxyethane, 1,4-dioxane; miscellaneous: dimethyl formamide, acetone, benzene, toluene, chloroform, methylene chloride.

Percent Water/Organic Solvent Variations

Figure 12B:
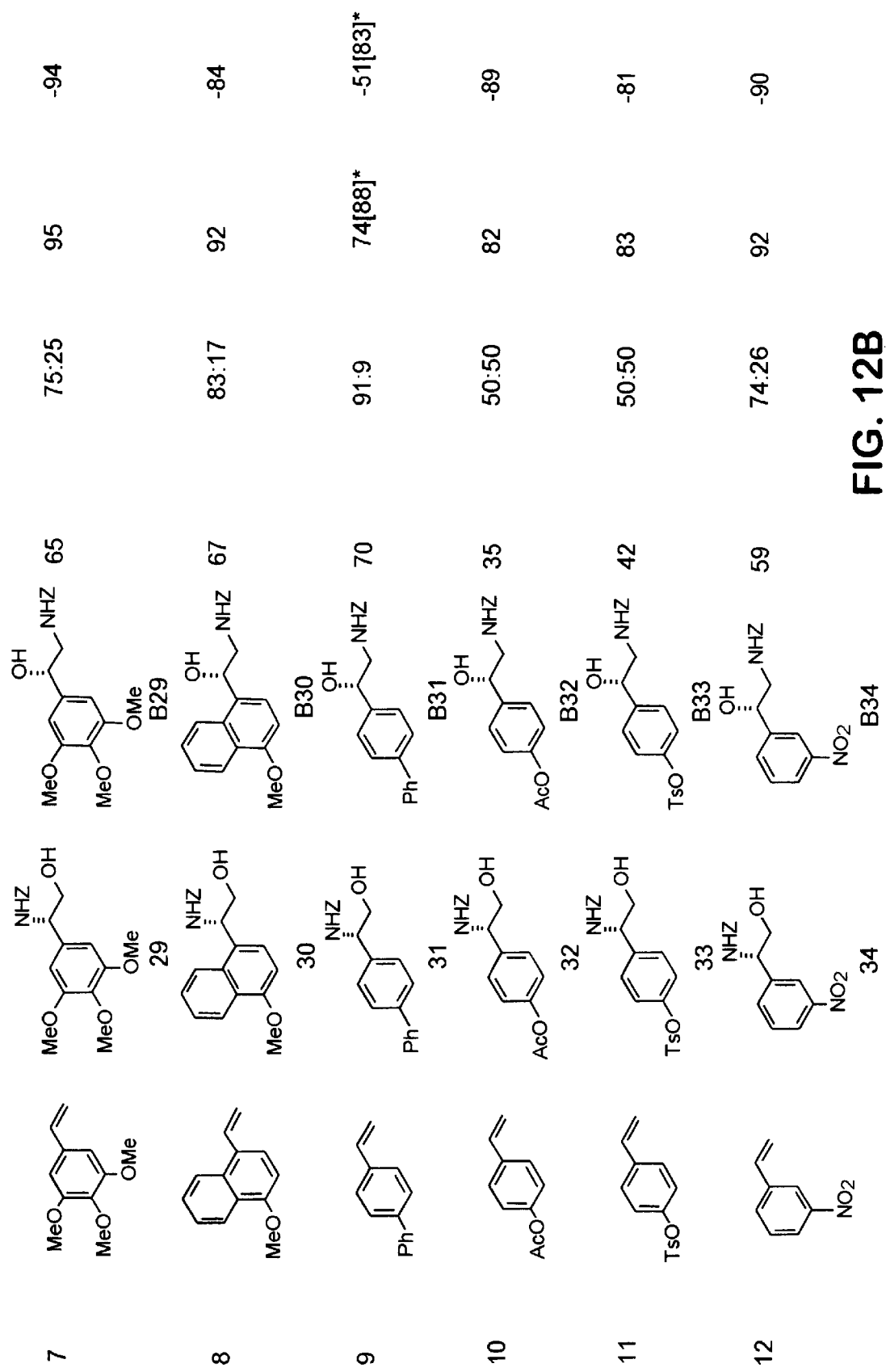
FIG. 12 shows a table of formed compounds using the AA reaction and BnOC(O)NNaCl as the nitrogen source wherein [a] All reactions were performed on 2.0 mmol scale using 4% K2OsO2(OH)4 5%, ligand and n-PrOH/water (1:1) at 25° C. for 1 h. [b] The (S)-enantiomer of the benzylic amine regioisomer (A) is shown in each case. It is the enantiomer in excess when (DHQ)2PHAL is the ligand. [c] Isolated yield of A using (DHQ)2PHAL. [d] Ratio of benzylic amine A/benzylic alcohol B regioisomers determined by 1H NMR. [e] Determined by chiral HPLC (using chiralcel AD column). [f] The "negative" ee values are meant to emphasize that with (DHQD)2PHAL as ligand the mirror image isomer dominates (i.e. A>ent-A). [*] Ee-values after one crystallization. [**] Yield based on starting material recovered.
Figure 12C:
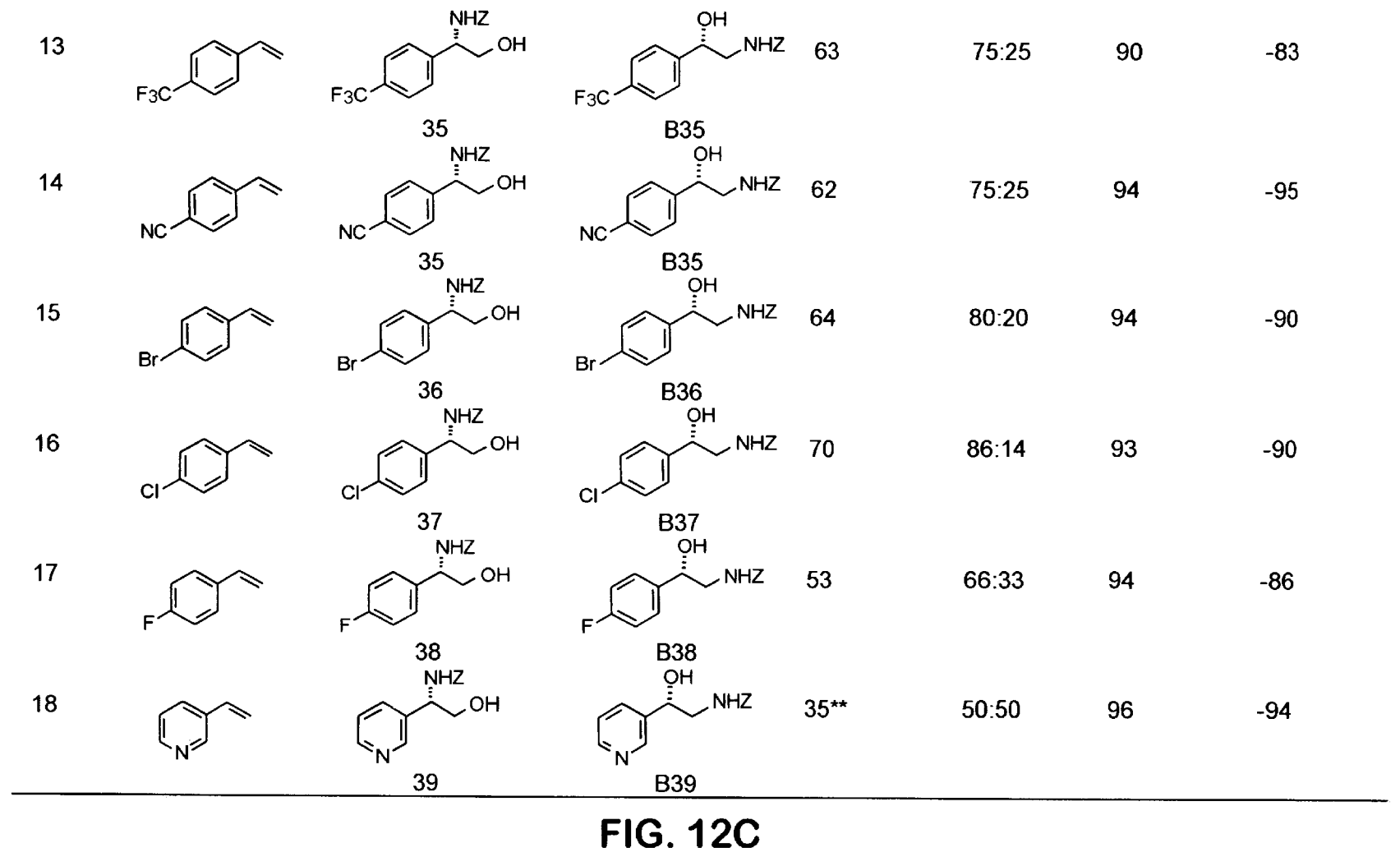

Two key points are that the ee and especially the yields are lower in the low water range (see FIGS. 11 and 12). No reaction is seen with only 2 to 4 equiv of water present which must be much less than 0.1% water These same "minuscule" amounts of water" conditions work great for the silver and mercury salts of the N-chlorocarbamates in the old catalytic aminohydroylation process with no chiral ligands present.

Solvent Concentration Variations,

In its present form the process starts to give lower selectivities for some substrates when the concentration of olefin (which of course prescribes the standard concentration of all the other species) gets much above 0.1 molar.

Ligand Variations;

The ligand can range from ca. 1 to 10 mol % (less is appropriate for lower temperatures; eg. 1% might be enough at 0° C. and 10% would probably be needed to keep the % ee at reasonable levels if the temperature reaches 35 or 40° C. In practice, the molarity of the ligand matters and the amount of ligand needed to realize the "ceiling ee" scales directly with the reaction concentration (ie if twice the volume of solvent is used, then the mol % of ligand added must also double to keep its molarity constant and correspondingly if the reaction is run twice as concentrated as usual (see general recipe below) then half of the usual mol % ligand gives the needed ligand molarity). Because the crucial binding of the ligand is an extremely rapid bimolecular process, the equilibrium constant is highly sensitive to temperature which is why the molarity of ligand needed, increases rapidly with temperature.

Osmium Variations:

The amount of Os catalyst can range from 0.5% (probably even less in the very best cases, and in any case the number will drop as the process if further improved) to 10 or even 20%. The general procedure conditions uses 4% to have fast reaction times, but 2% is good for most cases. The high loadings of 20%, for example, is needed to achieve reasonable rates with very poor substrates (this conclusion follows from the extensive experience by us and others with the AD, where in desparate situations 20 or more % Os catalyst is needed.

Temperature Variations:

For most cases, the carbamate AA process is run between 10 and 25 degrees C. There may be cases where 0 degrees—up to 35 to 40 degrees may be advantageous depending on substrate.

Deprotection Conditions of Carbamate to Free Amine t-BOC: TFA procedure: Lundt et al *Int. J. Pept. Protein Res.*, 1978, 12, 258; HCl procedure: Stahl et al. *J. Org. Chem.*, 1978, 43, 2285.

Benzyl carbonate: Hydrogenation procedure: Bergman et al Ber., 1932, 65, 1192.

Ethyl and methyl carbamate: Trimethylsilyliodide procedure: Lott et al. *J. Chem. Soc. Chem. Comm* 1979, 495; HBr procedure: Wani et al *J. Am. Chem. Soc.*, 1972 94, 3631.

Transformation of R—COOH to R—COOMe

Procedure as adapted from Chan et al. *Synthesis* 1983, 201.

Syntheses of a Representative Set of Hydroxycarbamates

Synthesis of Compound 1

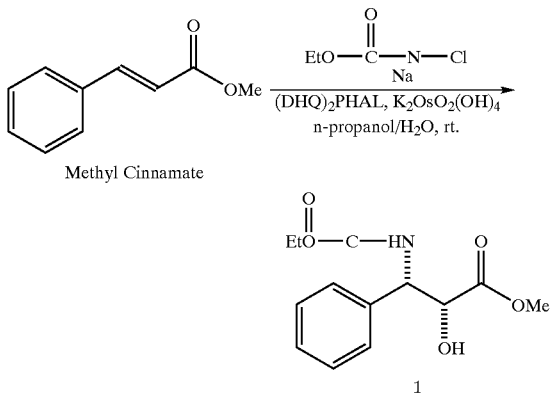

Methyl Cinnamate

1

To a solution of NaOH (0.112 g, 3.05 mmol) in 7.5 mL of water was added ethyl carbamate (0.276 g, 3.10 mmol). The resulting solution was stirred at room temperature for 10 min and then t-butyl hypochlorite (0.331 g, 3.05 mmol; Aldrich Chemical) was added dropwise. The above solution was stirred for another 10 min and then 7.5 mL of n-propanol and $(DHQ)_2$-PHAL (40 mg, 0.05 mmol, 5 mol %) were added to form a homogeneous solution. The reaction mixture was immersed in a room temperature bath and added methyl cinnamate (0.162 g, 1 mmol) and $K_2OsO_2(OH)_4$ (14.7 mg, 0.04 mmol, 4 mol %) were then added. The reaction was stirred for 45 min with the color changing from light green to light yellow, followed by quenching by addition of aqueous sodium sulfite (sat. 6 mL); the phases were separated, and the aqueous phase was extracted with ethyl acetate (3×5 mL). The combined organic extracts were washed with water and brine, dried over $MgSO_4$ and the solvent concentrated to give the crude product, which also contained the ethyl carbamate by-product produced upon the reduction of the excess N-chlora-N-sodiocarbamate. Flash chromatography (6:4:1 hexane/$CHCl_3$/MeOH) of this material provided 0.21 g (78% yield, >99% ee) of (2R,3S) vicinal hydroxycarbamate product.

If benzyl carbamate was used, 4 mL of n-propanol was added with water to dissolve all of benzyl carbamate before adding t-butyl hypochlorite.

Synthesis of Compound 2

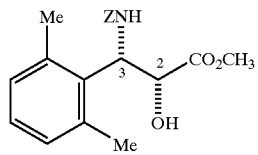

2

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and $(DHQ)_2$-PHAL (5 mol %) were added to form a homogeneous solution. The reaction mixture was immersed in a room temperature bath and then 2',6'-dimethyl cinnamate (1 equivalent; Aldrich) and $K_2OsO_2(OH)_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over $MgSO_4$ and the solvent was concentrated to give the crude product, which also contained the ethyl carbamate by-product produced upon the reduction of the excess N-chlora-N-sodiocarbamate. Flash chromatography (6:4:1 hexane/$CHCl_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 3

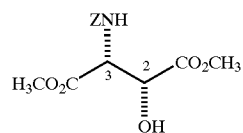

3

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and $(DHQ)_2$-PHAL (5 mol %) were added to form a homogeneous solution. The reaction mixture was immersed in a room temperature bath and then dimethylfumarate (1 equivalent; Aldrich) and $K_2OsO_2(OH)_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over $MgSO_4$ and the solvent was concentrated to give the crude product, which also contained the ethyl carbamate by-product produced upon the reduction of the excess N-chlora-N-sodiocarbamate.

Flash chromatography (6:4:1 hexane/$CHCl_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 4

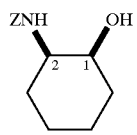

4

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and the n-propanol (0.13 Molar; based on initial olefin concentration) and $(DHQ)_2$-PHAL (5 mol %) were added to form a homogeneous solution. The reaction mixture was immersed in a room temperature bath and then cyclohexene (1 equivalent; Aldrich) and $K_2OsO_2(OH)_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over $MgSO_4$ and the solvent was concentrated to give the crude product, which also contained the ethyl carbamate by-product produced upon the reduction of the excess N-chlora-N-sodiocarbamate. Flash chromatography (6:4:1 hexane/$CHCl_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 5

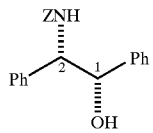

5

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and $(DHQ)_2$-PHAL (5 mol %) were added to form a homogeneous solution. The reaction mixture was immersed in a room temperature bath and then trans-stilbene (1 equivalent; Aldrich) and $K_2OsO_2(OH)_4$ (4 mol %) were then added. The reaction was stirred for 45 minutes at room temperature with the color changing from light green to light yellow, followed by quenching by addition of aqueous sodium sulfite saturated 0.17 Molar; based on initial olefin concentration). The phases were separated, and the aqueous phase was extracted with ethyl acetate (3×0.20 M volumes). The combined organic extracts were washed with water and brine, dried over $MgSO_4$ and the solvent was concentrated to give the crude product, which also contained the ethyl carbamate by-product produced upon the reduction of the excess N-chlora-N-sodiocarbamate. This is on example of a solution-to-solid and solid-to-solid entry—the work-up required simple filtration which provided the vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 6

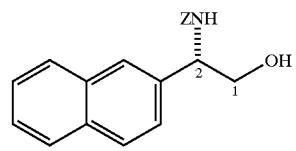

6

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and $(DHQ)_2$-PHAL (5 mol %) were added to form a homogeneous solution. The reaction mixture was immersed in a room temperature bath and then trans-stilbene (1 equivalent; Aldrich) and $K_2OsO_2(OH)_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over $MgSO_4$ and the solvent was concentrated to give the crude product, which also contained the ethyl carbamate by-product produced upon the reduction of the excess N-chlora-N-sodiocarbamate. This is an example of a solution-to-solid and solid-to-solid entry—the work-up required simple filtration which provided the vicinal hydroxycarbamate products.

If benzyl carbamate was used, an additional 0.25 M volume of n-propanol was added with water to dissolve all of benzyl carbamate before adding t-butyl hypochlorite.

Synthesis of Compound 7

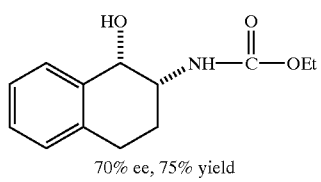

7

70% ee, 75% yield

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13

Molar; based on initial olefin concentration) and (DHQ)$_2$-PHAL (5 mol %) were added to form a homogeneous solution. The reaction mixture was immersed in a room temperature bath and then 1,2-dihydronaphthalene (1 equivalent; Aldrich) and K$_2$OsO$_2$(OH)$_4$ (4 mol %) were then added. The reaction was stirred or 45 minutes at room temperature with the color changing from light green to light yellow, followed by quenching by addition of aqueous sodium sulfite saturated 0.17 Molar; based on initial olefin concentration). The phases were separated, and the aqueous phase was extracted with ethyl acetate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 8

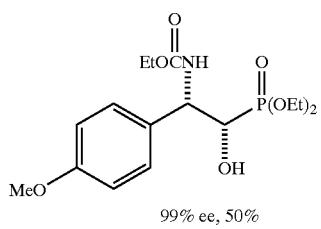

99% ee, 50%

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL. (5 mol %) were added to form a homogeneous solution. The reaction mixture was immersed in a room temperature bath and then trans-diethyl p-methoxy styryl phosphonate (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 9

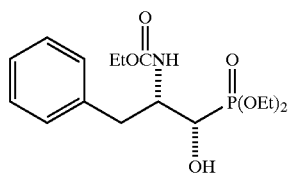

74% ee, 50%

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then trans-diethyl 3-phenyl propenyl phosphonate (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl activate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 10

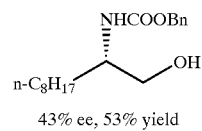

43% ee, 53% yield

To a solution of NaOH (3.05 equivalents) in water (0.13 Molar; based on initial olefin concentration) was added ethyl carbamate (3.10 equivalents). The resulting solution was stirred at room temperature for 10 minutes and then n-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL, (5 mol %) were added to form a homogeneous solution. The reaction mixture was immersed in a room temperature bath and then 1-decene (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 11

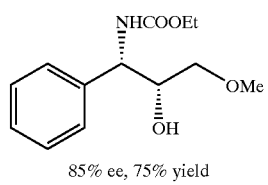

85% ee, 75% yield

To a solution of NaOH (3.05 equivalents) in water (0.13 Molar; based on initial olefin concentration) was added ethyl cabamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then cinnamyl alcohol methyl ether (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 12

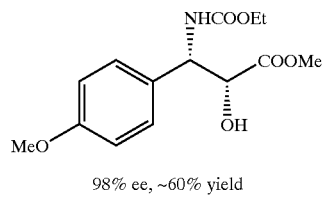

98% ee, ~60% yield

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then methyl trans 4-methoxycinnamate (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydoxycarbamate product.

If benzyl carbamate was used, an additional 0.25 M volume of n-propanol was added with water to dissolve all of benzyl carbamate before adding t-butyl hypochlorite.

Synthesis of Compound 13

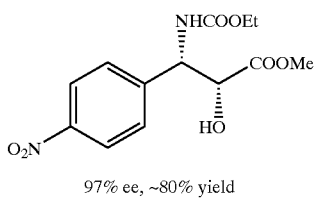

97% ee, ~80% yield

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then methyl-trans-4-nitrocinnamate (1 equivalent) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 14

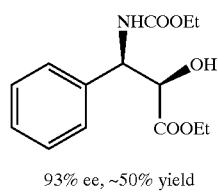

93% ee, ~50% yield

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then ethyl cis cinnamate (1 equivalent) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of (2R,3S)-(+)-Methyl-N-(p-toluenesulfonyl)-2-hydroxy-3-amino-3-phenyl-propionate in t-BuOH

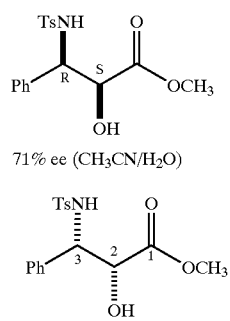

71% ee (CH$_3$CN/H$_2$O)

Compound 15.

To a 2 L round-bottom flask, equipped with a mechanical stirrer and a thermometer, was added (DHQ)-PHAL (6.6 g, 2.5 mol %), t-BuOH (600 mL) and H$_2$O (600 mL). The flask was immersed in a room temperature water bath. To the resulting homogeneous solution was added in order 290.4 g (1.01 mol) of Chloramine-T trihydrate (ca. 4/5 of the total added which is in 338 g, 1.18 mol), methyl cinnamate (27.2 g, 167.6 mmol, half of the total amount of olefin, which is 54.4 g, 0.33 mol; Aldrich chemical company) and potassium osmate(VI; Aldrich) (2.5 g, 2.0 mol %). As the reaction was stirred, the color changed from yellow to green in 15 min and then back to yellow after 90 min; TLC(EtOAc/Hexane, v/v=4/6) revealed that the disappearance of olefin coincided with the return of the yellow color. The flask was then immersed in an ice bath (0° C.) for 20 min. (During this cooling, the crystals of precipitated product made their first appearance.) To this cold, stirred suspension the remainder of the Chloramine-T trihydrate (48.4 g, 0.168 mol) and the second portion of methyl cinnamate (13.6 g, 84 mmol) was added. The ice bath was replaced by the room temperature water bath, and the new olefin charge was consumed in about 45 min during which time the color changed as before from yellow to green and back to yellow again. The resulting mixture was cooled back to 0° C. for over 15 min and the third and last portion of methyl cinnamate (13.6 g, 84 mmol) was added. The reaction was returned to the room-temperature water bath and the remaining olefin was consumed in about 45 min with the above noted sequence of color changes. The flask was again immersed in an ice bath (0° C.) for about 20 min. Essentially all of the product precipitated out of solution and was isolated by filtration, washed twice with cold (ca 0° C.) 100 mL portions of t-BuOH/H$_2$O (v/v=1/1) to yield 81.1 g of (2R,3S)-(+)-methyl-N-(p-toluenesulfonyl)-2-hydroxy-3-amino-3-phenyl propionate (2) (69% yield, 82% ee, m.p. 147–148° C.; for racemic: m.p. 125–126° C. 4c).

A 6.3 g portion of this crude 2 was triturated with EtOAc at room temperature (1×75 mL, 1×35 mL and 2×20 mL), the solid triturand of 2 remaining after these triturations is of low ee and is discarded. Concentration of the combined triturates afforded 5.3 g of enantiomerically enriched 15 (58% yield, 92% ee), three recrystallizations from MeOH gave 3.2 g of enantiomerically pure product (35% yield based on 1), m.p. 154–155° C.; [a]\o(25,D)=+19.8° (c 0.5, 95% EtOH); $^1$H NMR (400 MHz, DMSO/D$_2$O) δ 2.23 (s, 3H), 3.45 (s, 3H), 4.17 (d, J=4.0 Hz, 1H), 4.65 (d, J=4.0 Hz, 1H), 7.08–7.19 (m, 8H), 7.40 (d, J=8.2 Hz, 2H); $^{13}$C NMR (100 MHz, DMSO) δ 171.8, 141.9, 138.4, 138.7, 128.9, 327.6, 127.3, 126.9, 126.4, 74.4, 60.1, 51.6, 20.9.

Synthesis of (2R,3S)-(+)-Methyl-N-(p-toluenesulfonyl)-2-hydroxy-3-amino-3-phenyl-propionate (15) in n-Propanol

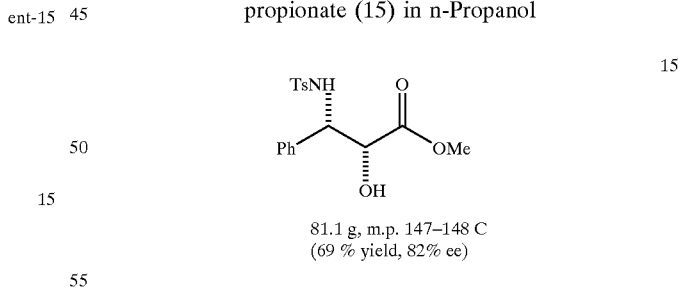

81.1 g, m.p. 147–148 C
(69 % yield, 82% ee)

To a solution of (DHQ)$_2$-PHAL (2.20 g, 2.80 mmol, 5 mol %) in n-Propanol (100 mL) and water (100 ml) in 500 mL Erlenmeyer or round-bottomed flask were added in order, methyl cinnamate (9.08 g, 56.0 mmol), Chloramine-T trihydrate (48.4 g, 0.168 mol, 3.0 eq) and K$_2$OsO$_2$(OH)$_4$ (0.824 g, 2.24 mmol, 4 mol %). The reaction flask was immersed in a room-temperature water bath and the slurry stirred for 3 hr. Over the course of the reaction, the color changed from brown to deep green and then back to yellow as hydroxysulfonamide product appeared as white precipitates. The flask was then immersed in an ice bath (0° C.) for 20 min. During this cooling, almost all of crystalline hydroxysulfonamide product precipitated from the reaction solution. The product was isolated by filtration and the crude solid was washed once with cold (ca 5° C.) 1:1 n-Propanol/H$_2$O (15 mL) to yield 11.7 g of (2R,3S)-(+)-methyl-N-(p-toluenesulfonyl)-2-hydroxy-3-amino-3-phenyl propionae (60% yield, 89% ee).

Synthesis of (2R,3S)-2-Hydroxy-3-amino-3-phenylpropionic Acid (16)

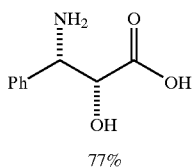

77%

Compound 16.

A heavy-walled borosilicate pressure bottle was charged with the enantiomerically enriched (92% ee) 15 [i.e. the triturated but not recrystallized material (vide supra)] (1.25 g, 3.6 mmol), phenol (1.04 g, 11.1 mmol) and excess 33% hydrogen bromide in acetic acid (20 mL, 0.117 mol, Acros). The bottle was sealed with a bushing, having a Teflon-lined cap, before being immersed completely in an oil bath. The bath was maintained at 75° C. for 10–12 h. The resulting solution was then concentrated in vacuo to about 10 mL (water pump followed by an oil pump which was protected by a 0° C. aqueous KOH bubbler). The crude solution was purified by ion-exchange chromatography (Amberlite IR-120 resin, 35 g), elueting with 80 mL of water (to remove impurities), then with 80 mL of 10% ammonium hydroxide (start with a dilute solution due the heat generated in the ion exchange process) followed by 80 mL of 40% ammonium hydroxide. Collection of the ammonium hydroxide eluate gave a solution of the ammonium salt of 3 which upon lyophilization yielded pure (2R,3S)-2-hydroxy-3-amino-3-phenylpropionic acid (37, 0.51 g, 77%). m.p. 235° C., decomp. (literature: Deng et. al J. Org. Chem. 57, (1992), 4320: m.p. 238° C., decomp.); rotation after conversion to the hydrochloride salt is [a]\o(25,D)=–14.5° (c 0.37, MeOH; [a]\o(25,D) –15.1° c 0.365, MeOH). 1H NMR (400 MHz, D$_2$O) δ 4.09 (d, J=6.0 Hz, 1H), 4.32 (d, J=6.0 Hz, 1H), 7.21–7.41 (m, 5H); $^{13}$C NMR (100 MHz, D$_2$O/DMSO) d 177.7, 135.4, 130.9, 130.7, 128.9, 75.0, 59.0.

N-Benzoyl-(2R,3S)-2-hydroxy-3-amino-3-phenylpropionic Acid (17)

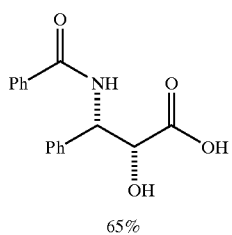

65%

Compound 17.

The enantiomerically enriched olefin (0.43 g, 2.37 mmol) was converted to N-benzoyl-(2R,3S)-2-hydroxy-3-amino-3-phenylpropionic acid (4, 0.44 g, 65%) according to our earlier Schotten-Baumann-based procedure for this same transformation (Sharpless et al. J. Org. Chem. 59 (1994), 5104). Chemically and enantiomerically pure 4 was isolated by simple filtration of the solid which appeared when the pH of the reaction mixture was adjusted to ca. 2 by addition of aqueous HCl. m.p. 166–167° C. (lit: Ojima et al. J. Org. Chem 56 (1991) 1681: 167–169° C.); [a]\o(25,D) –34.0° (c 0.50, EtOH) (lit: Sharpless et al. J. Org. Chem. 1976, 41, 177: [a]\o(25,D) –35.9° c 0.565, EtOH); lit3d [a]\o(25,D) –35.5° (c 1.07, EtOH); 1H NMR (400 MHz, DMSO) δ 4.37 (d, J=4.3 Hz, 1H), 5.46 (dd, J=8.8, 4.2 Hz, 1H), 7.22–7.55 (m, 9H), 7.84 (d, J=7.2 Hz, 1H), 8.60 (d, J=8.9 Hz, 1H), 12.73 (br, 1H); $^{13}$C NMR (100 MHz, DMSO) δ 173.5, 166.0, 140.3, 134.4, 131.4, 128.4, 128.0, 127.4, 127.2, 126.9, 73.6, 55.8.

GENERAL PROCEDURE 1

Catalytic Asymmetric Aminohydroxylation in 1:1 Acetonitrile/Water (Used for Synthesis of Compounds 1–17)

Figure 1:
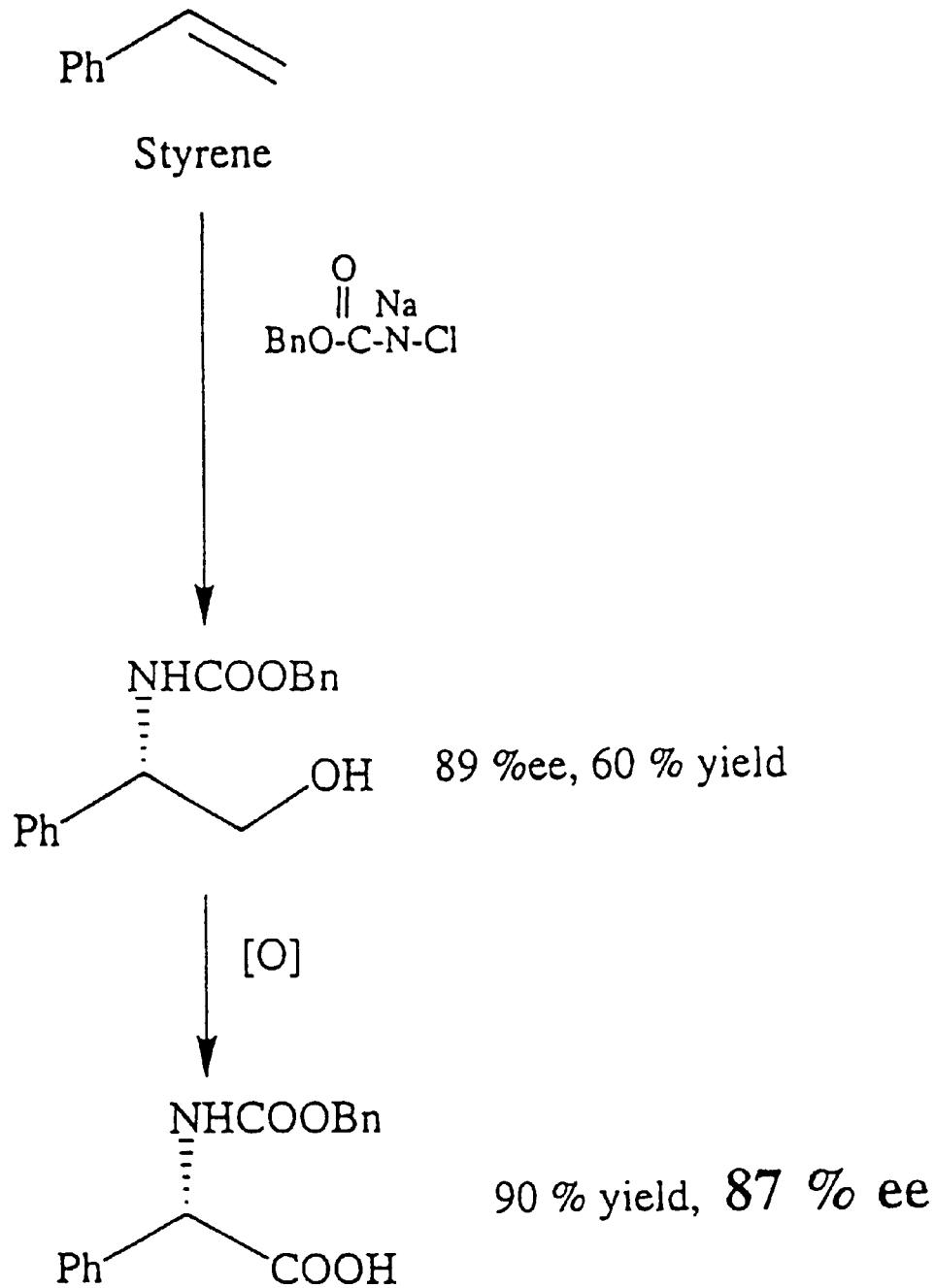
FIG. 1 illustrates the asymmetric aminohydroxylation of styrene to its corresponding α-hydroxy-β-benzylcarbamate. The α-hydroxy-β-benzylcarbamate is subsequently oxidized to the amino acid. Oxidation conditions include, but are not limited to: $RuCl_3$, $H_5IO_6$ oxidation to free acid: Sharpless et al *J. Org. Chem.* 3937 (46), 1981; $KMnO_4$/NaOH: Garner et al., Tetrahedron Lett., 5855–58, 1984; $RuO_2$: Martin, Tetrahedron Lett., 2701–02, 1988. $K_2CrO7/H_2SO_4$: J. Am Chem. Soc., 2498, 1960; PtO2: *J. Org., Chem.* 4898, 1987.
Figure 2:
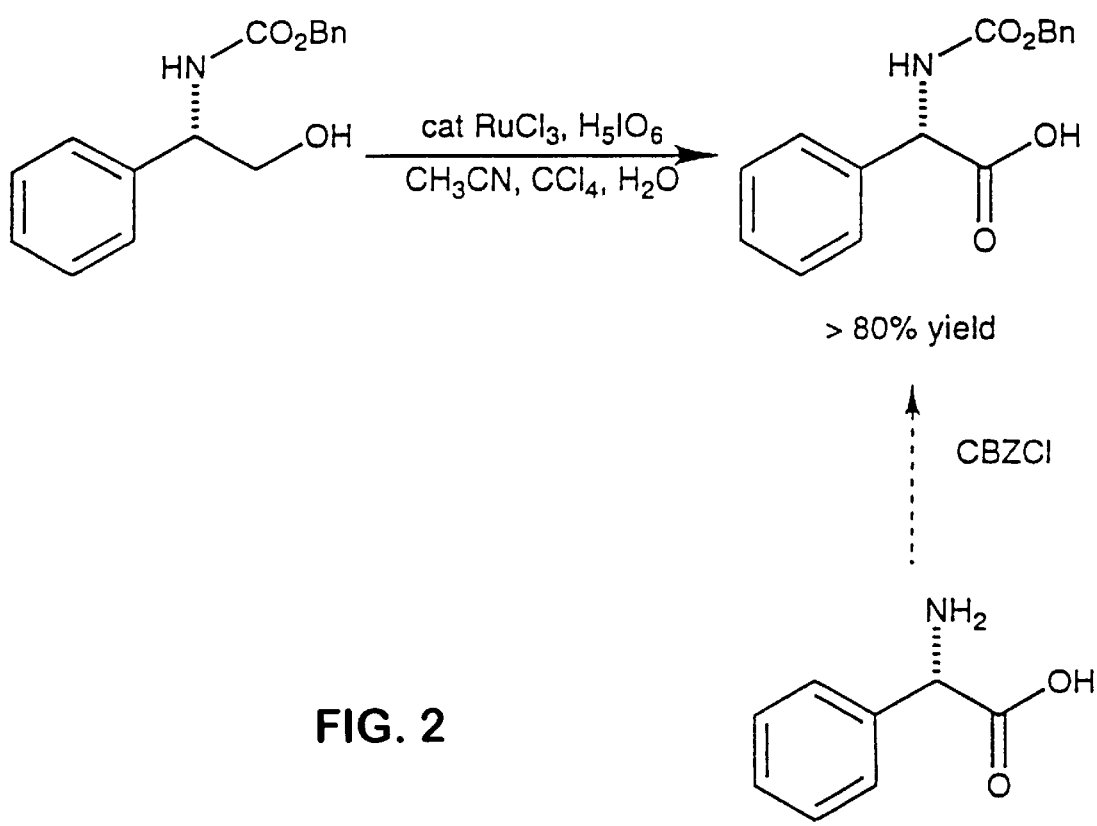
FIG. 2 illustrates the oxidation of the α-hydroxy-β-benzylcarbamate derived from styrene (see FIG. 1). Conditions include, but are not limited to: $RuCl_3$, $H_5IO_6$ oxidation to free acid: Sharpless et al *J. Org. Chem.* 3937 (46), 1981; $KMnO_4$/NaOH: Garner et al., Tetrahedron Lett., 5855–58, 1984; $RuO_2$: Martin, Tetrahedron Lett., 2701–02, 1988. $K_2CrO7/H_2SO_4$: J. Am Chem. Soc., 2498, 1960; PtO2: *J. Org. Chem.* 4898, 1987. If a tertbutylcarbamate is used in the asymmetric aminhydroxylation, the nitrogen is subsequently protected as a CBZ (carbobenzyloxy) group which can be independently obtained by protection of phenylalanine (dashed arrow).
Figure 3:
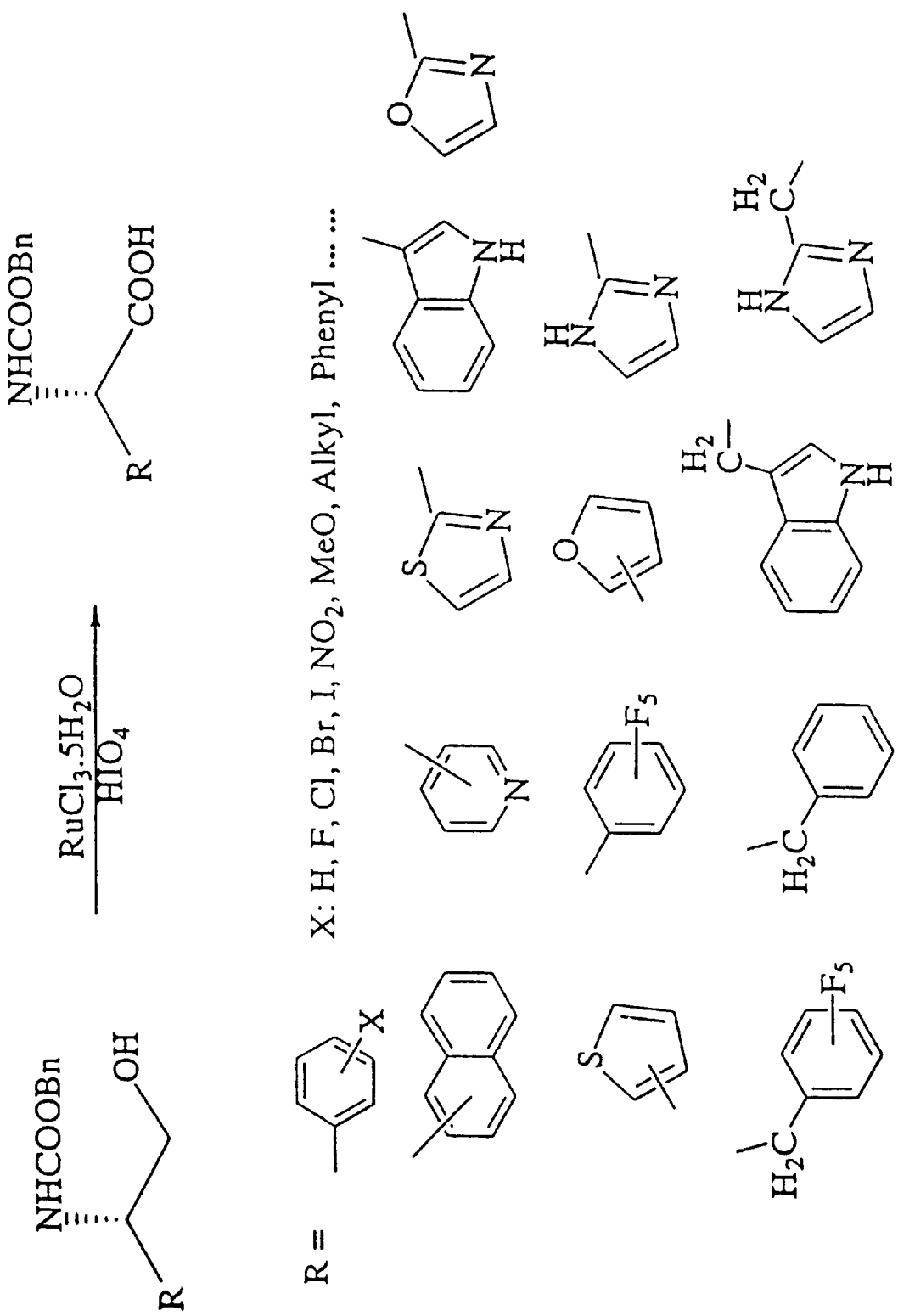
FIG. 3 illustrates oxidation conditions to the protected amino acid from the carbamate (benzyl carbamate is shown, however other carbamates commonly used in the AA procedure are possible) with indicated aromatic and heteroaromatic "R" groups.
Figure 4:
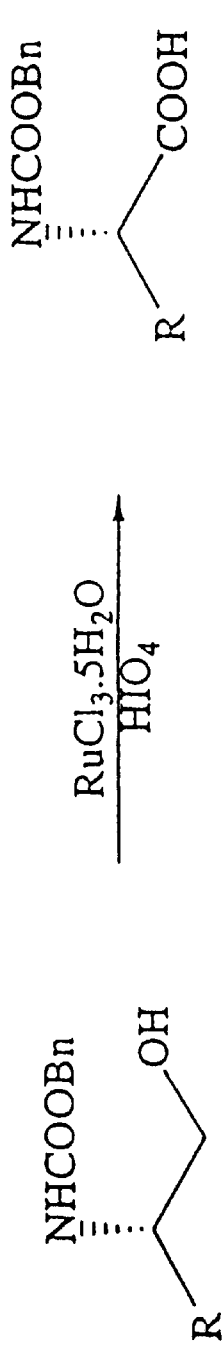
FIG. 4 illustrates oxidation conditions to the protected amino acid from the carbamate (benzyl carbamate is shown, however other carbamates commonly used in the AA procedure are possible) with indicated nonaromatic "R" groups.
Figure 5:
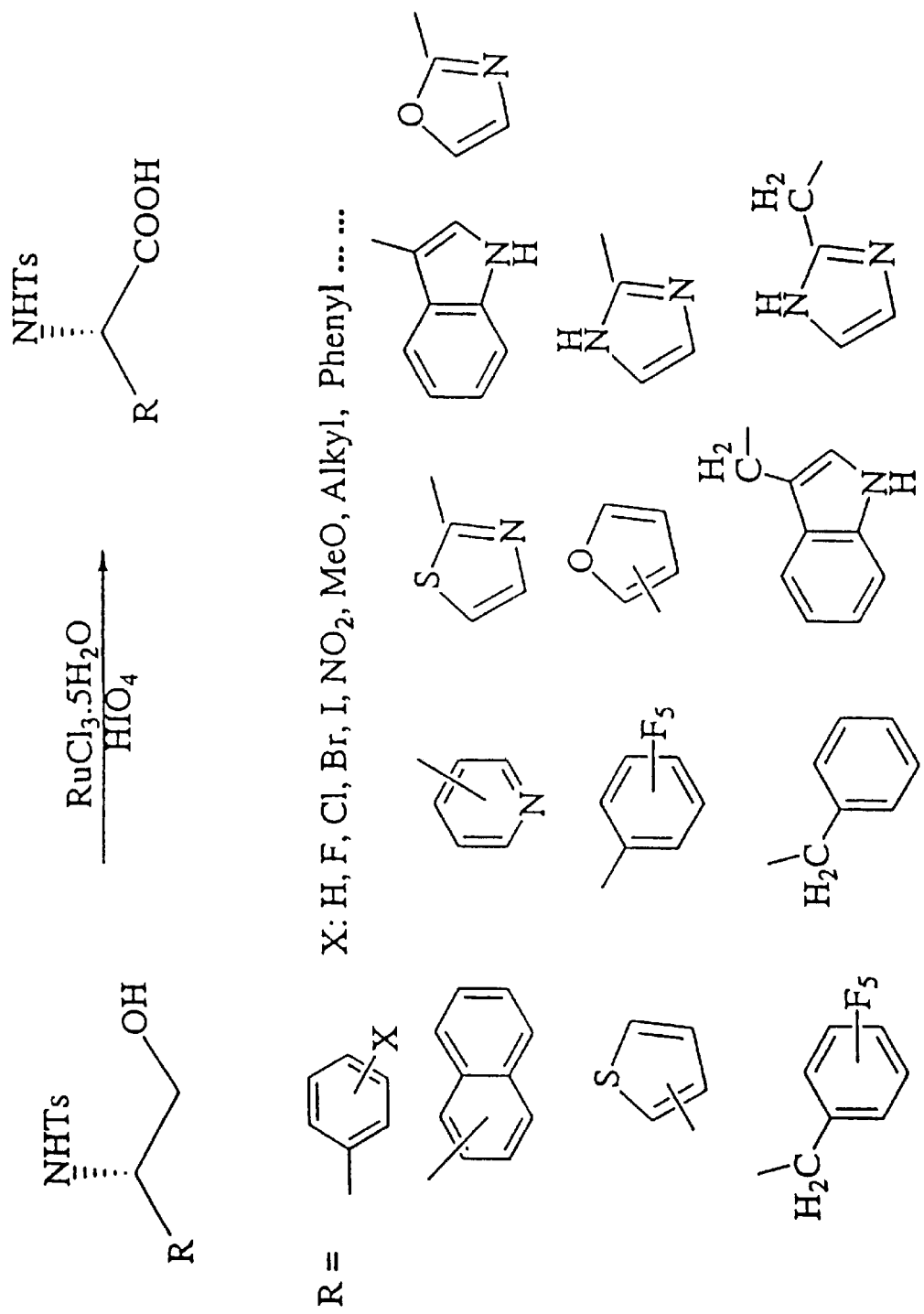
FIG. 5 illustrates oxidation conditions to the protected amino acid from the sulfonamide (tosyl (Ts) sulfonamide is shown, however other sulfonamides commonly used in the AA procedure are possible) with indicated aromatic and heteroaromatic "R" groups.
Figure 6:
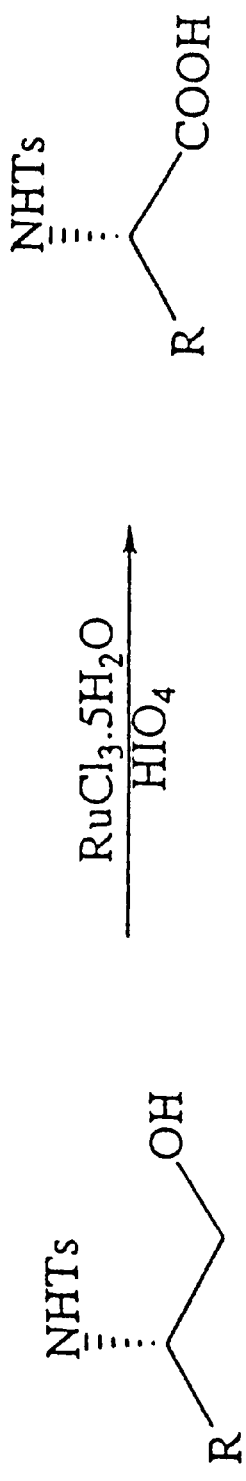
FIG. 6 illustrates oxidation conditions to the protected amino acid from the sulfonamide (tosyl (Ts) sulfonamide is shown, however other sulfonamides commonly used in the AA procedure are possible) with indicated nonaromatic "R" groups.
Figure 7:
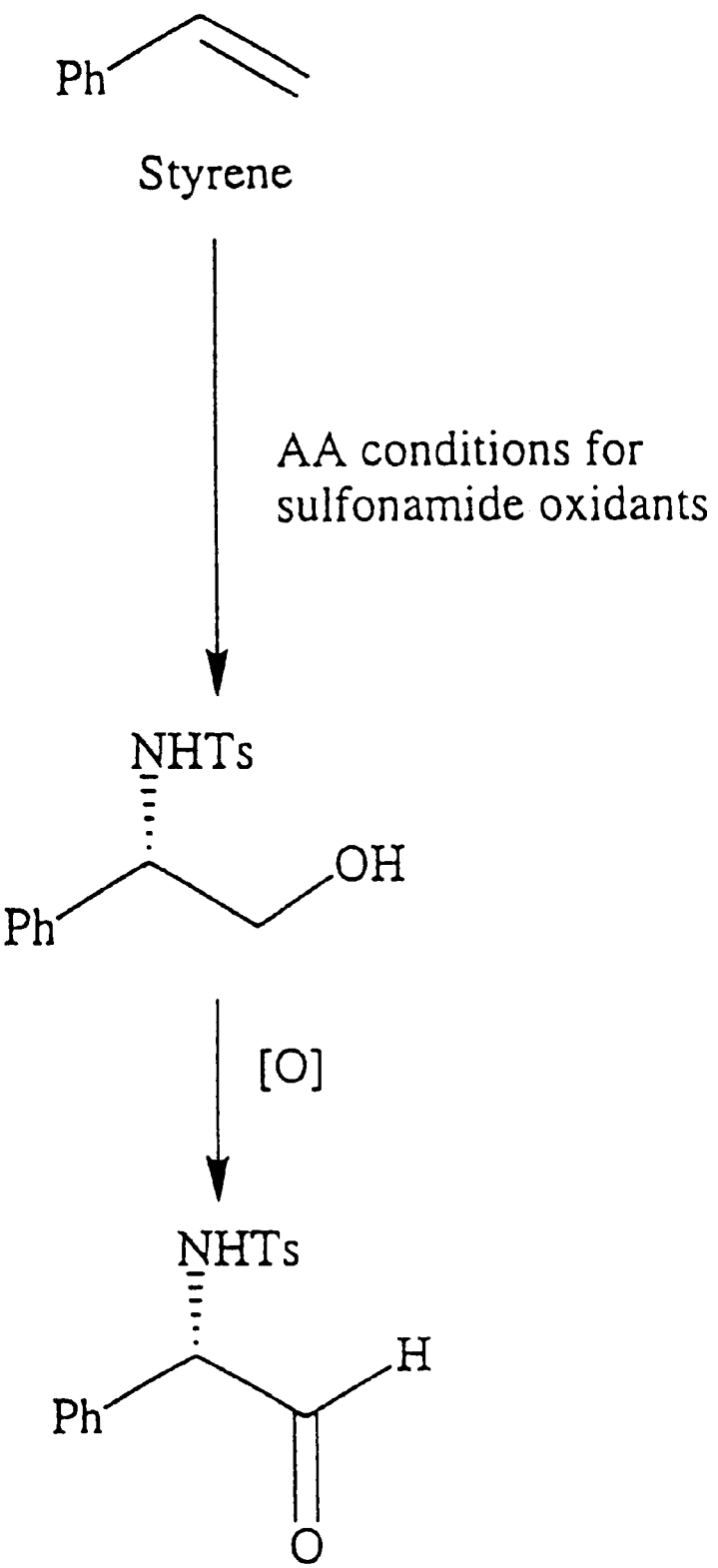
FIG. 7 illustrates the oxidation of the α-hydroxy-β-sulfonamide derived from styrene. Oxidation conditions include, but are not limited to oxidations well renown in the art, including TEMPO, Swern, $SO_3$/pyridine or PCC oxidations, to achieve the aldehyde.
Figure 8:
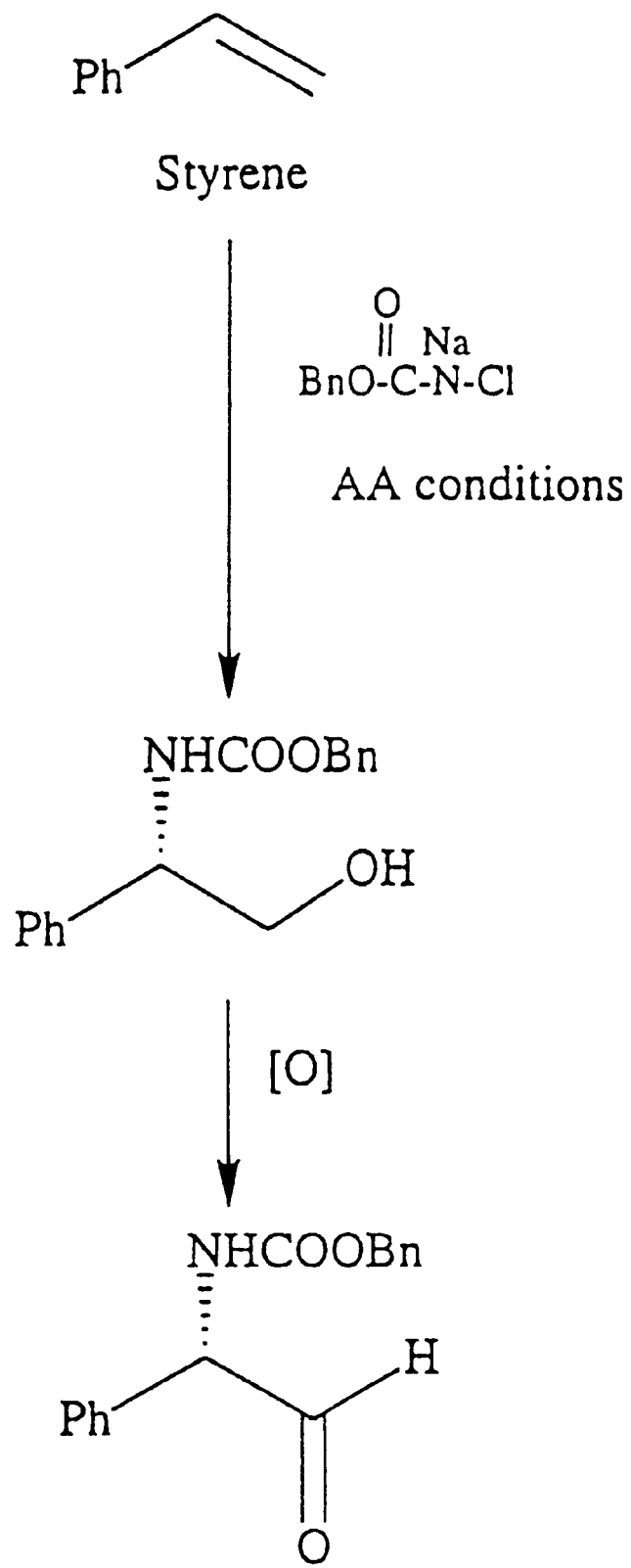
FIG. 8 illustrates the oxidation of the α-hydroxy-β-benzylcarbamate derived from styrene. Oxidation conditions include, but are not limited to oxidations well known in the art, including TEMPO, Swern, $SO_3$/pyridine or PCC oxidations, to achieve the aldehyde.

To a stirred solution of (DHQ)$_2$-PHAL (0.11 g, 0.14 mmol, 5 mol %) in 20 mL of acetonitrile and 20 mL of water, in any convenient-sized glass vessel or vial, was added desired olefin (all commercially available from Aldrich, 2.8 mmol), Chloramine-T trihydrate (2.42 g, 8.4 mmol, 3 eq) and K$_2$OsO$_2$(OH)$_4$ (41.6 mg, 0.112 mmol, 4 mol %). As the reaction proceeded to completion over the course of about one and half hours at room temperature, the color of the solution changed from yellow to pale green, then deep green and finally back to yellow (for entry 3 in Table 1, the yellow color remains throughout). After addition of aqueous sodium sulfite (1.0 g in 15 mL H$_2$O), the phases were separated, and the aqueous phase extracted with ethyl acetate (3×15 mL). The combined organic extracts were washed with brine, dried over MgSO$_4$ and the solvent concentrated to give the crude product, which also contains the p-toluenesulfonamide by-product produced upon the reduction of the excess Chloramine-T. In the case of the ethyl crotonate derivative, product 5, flash chromatography (6:4:1 hexane/CHCl3/MeOH) of this material provided 0.44 g (52% yield, 74% ee) of (2R,3S)-ethyl-N-(p-toluenesulfonyl)-2-hydroxy-3-amino-butanoate (5) as a clear oil eluting before the p-toluenesulfonamide impurity (52% yield, 74% ee). Similar purification provides compounds 2, 6, 7, 8 and 9. with the indicated yields and conditions shown in FIG. 4. NOTE: Replacement of the 3 eq of Chloramine-T with 1.5 eq of Chloramine-T and 1.5 eq of Et$_4$NOAc gives comparable results and reduces the amount of p-toluenesulfonamide by-product formed. This can greatly simplify product isolation, especially in cases where the product and the toluenesulfonamide have similar chromatographic mobilities.

GENERAL PROCEDURE 2

Catalytic Asymmetric Aminohydroxylation in 1:1 TertButanol/Water (Used for Synthesis of Compounds 2, 7 or 8)

To a solution of (DHQ)2-PHAL (2.20 g, 2.80 mmol, 5 mol %) in t-BuOH (100 mL) and water (100 ml) in 500 mL Erlenmeyer or round-bottomed flask were added in order, desired olefin (56.0 mmol), Chloramine-T trihydrate (48.4 g, 0.168 mol, 3.0 eq) and K$_2$OsO$_2$(OH)$_4$ (0.824 g, 2.24 mmol, 4 mol %). The reaction flask was immersed in a room-temperature water bath and the slurry stirred for 2.5 hr. Over the course of the reaction, the color changed from brown to deep green and then back to yellow as the stilbene slurry became a hydroxysulfonamide slurry. The product was isolated by filtration and the crude solid was washed once with cold (ca 5° C.) 1:1 t-BuOH/H$_2$O (15 mL) to yield the product β-hydroxysulfonamide. In the case of product 7, 16.1 g of N-(p-toluenesulfonyl)-(1S,2S)-2-amino-1,2-diphenylethanol (7) (78% yield, 64% ee, pure by NMR and HPLC). Trituration of this product twice with ethyl acetate (2×15 mL) at room temperature in a sintered glass funnel gave enantiomerically pure 7 (10.3 g, 50% yield, >99% ee, mp 166–167° C.). See Sharpless, J. Org. Chem. 1994, 59, 5104 and Sharpless, J. Org. Chem. 1994, 59, 8302 for analogous solid-to-solid AD procedures.

Analysis of Enantiomeric Excesses for 2-9

Methyl cinnamate derivative 2: Chiralcel OG, 30% i-PrOH/hexane, 1 mL/min; 21.8 min (2S,3R), 28.3 min (2R,3S). Ethyl crotonate derivative 5: Chiralcel OD-H, 15% i-PrOH/hexane, 1 mL/min, 7.5 min (2S,3R), 13.4 min (2R, 3S). Dimethyl fumarate derivative 6: Chiralcel OG, 30% i-PrOH/hexane, 1 mL/min, 16.7 min (2S,3S), 21.8 min (2R,3R). trans-Stilbene derivative 5: Chiralcel OD-H, 15% i-PrOH/hexane, 1 mL/min, 16.2 min (1S,2S), 26.0 min (1R,2R). cis-Stilbene derivative 8: Chiralcel OD-H, 15% i-PrOH/hexane, 0.5 mL/min, 18.5 min (1S,2R), 22.1 min (1R,2S). Cyclohexene derivative 9: Chiralcel OG, 15% i-PrOH/hexane, 0.5 mL/min, 28.5 min (1S,2R), 34.4 min (1R,2S).

Correlation of the Absolute Configurations of 2-9

Methyl Cinnamate Derivative (2R,3S)-2:

Authentic (2R,3S)-2 was synthesized from N-benzoyl-(2R,3S)-3-phenylisoserine methyl ester (Taxol C-13 side chain; synthesis provided from Collet et al, Ecole normal superiure de Lyon, private communication) [6N HCl, reflux (remove methyl ester and N-benzoyl); SOCl$_2$, methanol (esterification); TsCl, K$_2$CO$_3$, 1:1 acetone/water (N-sulfonylation)] [HPLC: vide supra].

Ethyl crotonate derivative (2R, 3S)-18:

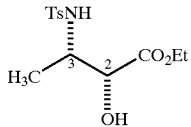

18

Compound 18:

(2R,3S)-15 was converted to N-tosyl-(2S)-alanine methyl ester [6N HCl (hydrolysis); RuCl$_3$/H$_5$IO$_6$ (oxidative cleavage); SOCl$_2$, methanol (esterification)] [HPLC: Chiralcel OD-H, 15% i-PrOH/hexane, 1 mL/min, 16.1 min (2R), 17.0 min (2S)].

Dimethyl fumarate derivative (2R, 3R)-19:

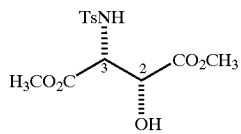

19

Compound 19:

(2R,3R)-19 was converted to its N-tosyl-(2R,3R)-2-oxazolidinone derivative which was independently synthesized from (1S,2S)-20 [carbonyl diimidazole, CH$_2$Cl$_2$; RuCl$_3$, H$_5$IO$_6$ (oxidative degradation of the phenyl groups); (Polt et. al. *J. Org. Chem.* 1992, 57, 5469), SOCl$_2$, methanol (esterification)] [HPLC: Chiralcel OD-H, 15% i-PrOH/hexane, 1 mL/min, 26.0 min (1R,2R), 47.2 min (1S,2S)].

trans-Stilbene derivative (1S, 2S)-20:

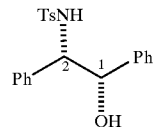

20

Compound 20:

An authentic sample of (1S,2S)-20 was synthesized from (1R,2S)-21 [CrO$_3$, H$_2$SO$_4$ (alcohol to ketone); DIBAL-H reduction gave a 4:1 mixture of (1R,2S)-21 to (1S,2S)-20] [HPLC: vide supra].

cis-Stilbene derivative (1S, 2R)-21:

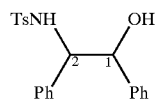

21

Compound 21:

An authentic sample of (1R,2S)-21 was synthesized from (1R,2S)-2-amino-1,2-diphenylethanol [TsCl, K2CO3, acetone/water] [HPLC: vide supra].

Cyclohexene derivative (1S, 2R)-22:

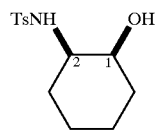

21

Compound 22:

N,N'-ditosyl-(1R,2R)-diaminocyclohexane was synthesized from (1S,2R)-19 [SO$_2$Cl$_2$, Et$_3$N, EtOAc; NaH (cyclic sulfamidate formation); NaN$_3$ (opening); H$_2$, Pd/C (azide reduction); TsCl, K$_2$CO$_3$, 1:1 acetone/water] and compared to the compound derived from authentic (1R,2R)-diaminocyclohexane [HPLC: Chiralcel AS, 20% i-PrOH/hexane, 1 mL/min, 23.2 min (1R,2R), 32.3 min (1S,2S)].

Catalytic Asymmetric Aminohydroxylation in 1:1 Tertbutanol/Water

To a solution of (DHQ)$_2$-PHAL (2.20 g, 2.80 mmol, 5 mol %) in t-BuOH (100 mL) and water (100 ml) in 500 mL Erlenmeyer or round-bottomed flask were added in order, desired olefin (methyl cinnamate, p-methoxy-methyl-cinnamate, p-bromo-ethyl-cinnamate, o-methyl-methyl-cinnamate 2,5-dimethyl-methyl-cinnamate or 2,5-dimethoxy-methyl-cinnamate; all commercially available from Aldrich) (56.0 mmol), Chloramine-T trihydrate (48.4 g, 0.168 mol, 3.0 eq) and K$_2$OsO$_2$(OH)$_4$ (0.824 g, 2.24 mmol, 4 mol %). The reaction flask was immersed in a room-temperature water bath and the slurry stirred for 2.5 hr. Over the course of the reaction, the color changed from brown to deep green and then back to yellow as the stilbene slurry became a hydroxysulfonamide slurry. The product was isolated by filtration and the crude solid was washed once with cold (ca 5° C.) 1:1 t-BuOH/H$_2$O (15 mL) to yield the product β-hydroxysulfonamide. Trituration of this product twice with ethyl acetate (2×15 mL) at room temperature in a sintered glass funnel gave enantiomerically pure β-hydroxysulfonamide compounds.

Catalytic Asymmetric Aminohydroxylation in 1:1:1 Ethanol/n-Propanol/Water (Used for Synthesis of Compound 11)

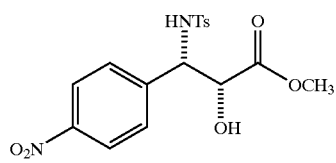

11: 94% ee
Regioselectivity:31:1
Yield: 86%

To a solution of (DHQ)$_2$-PHAL (2.20 g, 2.80 mmol, 5 mol %) in ethanol (63 mL) n-Propanol (63 mL) and water (63 ml) in 500 mL Erlenmeyer or round-bottomed flask were added in order, commercially available p-nitro methyl cinnamate derivative (10; Aldrich chemical company) (9.08 g, 56.0 mmol), Chloramine-T trihydrate (48.4 g, 0.168 mol, 3.0 eq) and K$_2$OsO$_2$(OH)$_4$ (0.824 g, 2.24 mmol, 4 mol %). The reaction flask was immersed in a room-temperature water bath and the slurry stirred for 5 hr. Over the course of the reaction, the color changed from brown to deep green and then back to yellow as hydroxysulfonamide product appeared as white precipitates. The flask was then immersed in an ice bath (0° C.) for 20 min. During this cooling, almost all of crystalline hydroxysulfonamide product precipitated from the reaction solution. The product was isolated by filtration and the crude solid was washed once with cold (ca 5° C.) 1:1 n-Propanol/H$_2$O (15 mL) to yield enantiomerically pure β-hydroxysulfonamide compound 11 in 86% overall yield and 94% ee.

Catalytic Asymmetric Aminohydroxylation in 1:1 n-Propanol/Water

To a solution of (DHQ)$_2$-PHAL (2.20 g, 2.80 mmol, 5 mol %) in n-Propanol (100 mL) and water (100 ml) in 500 mL Erlenmeyer or round-bottomed flask were added in order, commercially available methyl or ethyl cinnamate derivatives (Aldrich chemical company) (9.08 g, 56.0 mmol), Chloramine-T trihydrate (48.4 g, 0.168 mol, 3.0 eq) and K$_2$OsO$_2$(OH)$_4$ (0.824 g, 2.24 mmol, 4 mol %). The reaction flask was immersed in a room-temperature water bath and the slurry stirred for 3 hr. Over the course of the reaction, the color changed from brown to deep green and then back to yellow as hydroxysulfonamide product appeared as white precipitates. The flask was then immersed in an ice bath (0° C.) for 20 min. During this cooling, almost all of crystalline hydroxysulfonamide product precipitated from the reaction solution. The product was isolated by filtration and the crude solid was washed once with cold (ca 5° C.) 1:1 n-Propanol/H$_2$O (15 mL) to yield enantiomerically pure β-hydroxysulfonamide compounds.

Preparation of sulfonamides from sulfonychlorides

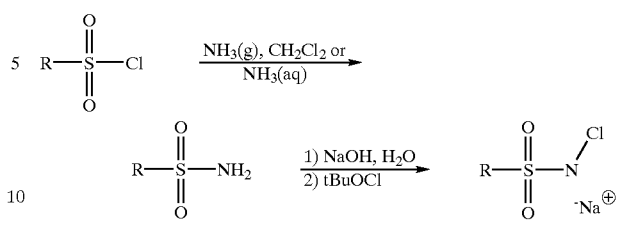

The sulfonyl chlorides used in the formation of the sulfonamides can come from commercially available sources such as Aldrich, Fluka, Sigma etc., or can be prepared from a procedure developed by Campbell et al. *Chem Rev*. 1978, 78, 65, for the preparation of N-chloro-N-sodiocarbamates which is a general procedure in the synthesis of N-chloro-N-sodio-aryl-and alkylsulfonamides. The sulfonyl chlorides (R—SO$_2$Cl) formed can include compounds where R=4-Me—Ph—, 4-MeOPh, Me, Ph—CH2—, 4-NO2—Ph—, 2-NO2—Ph—, 2-Naphthyl, 1-Napthyl, Dansyl or derivatives selected from the following functional groups: acyclic or cyclic hydrocarbons, hydroxyl compounds, ethers, protected amines, carbonyl compounds, esters or carboxylic acids, n-alkyl, alkynes pyrans, pyrrole), various heterocycles including: nitrites), pyrazines, pyrazoles, pyridazines, pyridines, pyrimidines, pyrrolizines, quinazolines, quionlines, thiophenes, silanes, CHnX where X=OR$_1$, halogens, aromatic rings, heterocycles, silyl groups and n=1 to 2.

Method A: Using a Sulfonyl Chloride (as Obtained Supra) and Gaseous NH$_{3(g)}$

NH$_3$ was bubbled (fritte or pipette) through well stirred CH$_2$Cl$_2$ (ca 100 ml) at RT. The sulfonyl chloride (100 mmol) was added in portions. After all of the sulfonyl chloride was added, stirring at RT under NH— was continued until TLC [hexane/ethylacetate] showed full conversion of the starting material. Precipitated NH4Cl was filtered off, the solvent was evaporated (NH$_3$) and the residue was crystallized from hot acetone/water and dried at high vaccum (oil pump, 0.1–0.01 torr) overnight to yield the crystalline, pure sulfonamides in nearly quantitative yields.

Method B: Using a Sulfonyl Chloride (as Obtained Supra) and Aqueous Ammonia

The sulfonylchloride (100 mmol) was added portionwise to a well stirred aqueous solution (100 ml) of NH3 (29.7%. Fisher) at RT. After all of the sulfonyl chloride was added, stirring at RT was continued for 2 more hours. The reaction mixture was slowly (NH$_3$!) heated to reflux and then cooled down to ca 4 C. The precipitated product was filtered off and crystallized from hot acetone/water and dried at high vaccum (oil pump, 0.1–0.01 torr) overnight to yield the crystalline, pure sulfonamides in nearly quantitative yields.

Trimethylsilylethyl sulfonamide and related akylsilylsulfonamides can be prepared according to a literature procedure: Steven M. Weinreb et al. Tetrahedron Lett. 1986, 27, 2099–2102.

General Catalytic Asymmetric Aminohydroxylation by in situ Generation of Chloramines Different from Chloramine T
(In Situ Generation of R—SO$_2$NClNa)

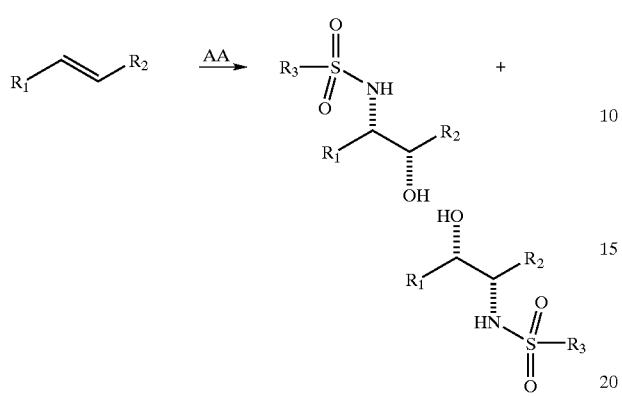

General Procedure:

T-butyl hypochlorite was slowly added to a well stirred solution of the desired sulfonamide (as obtained vida supra; 3.1 mmol, 3.1 eq) and 122 mg (3.05 mmol. 3.05 eq) of NaOH in 7.5 ml of water at room temperature. After 10 more minutes of stirring this solution was added dropwise to a solution of 40 mg (0.05 mmol, 0.05 eq) of (DHQ)$_2$Phal or (DHQD)$_2$Phal in 7.5 ml of MeCN (alternatively, a 1:1 mix of t-BuOH/water, n-propanol/water or 1:1:1 ethanol/n-propanol/water can be used, depending upon optimization conditions). Subsequently 190 mg (1.0 mmol, 1.0 eq) of substituted acrylates, esters or carboxylic acids. R$_2$=combination of R$_1$ R$_3$=4-Me—Ph—, 4-MeOPh, Me, Ph—CH2—, 4-NO2—Ph—, 2-NO2—Ph—, 2-Naphthyl, 1-Napthyl, Dansyl or derivatives selected from the following functional groups:acyclic or cyclic hydrocarbons, hydroxyl compounds, ethers, protected amines, carbonyl compounds, esters or carboxylic acids, n-alkyl, pyrans, pyrroles, various heterocycles including: pyrazines, pyrazoles, pyridazines, pyridines, pyrimidines, pyrrolizines, quinazoines, quionlines, thiophenes, silanes, CHnX where X=OR$_1$, halogens, aromatic rings, heterocycles, silyl groups and n=1 to 2 (reagents commercially or synthetically available) and 14.7 mg (0.04 mmol, 0.04 eq) of K$_2$OsO$_2$(OH)$_4$ were added and the reaction mixture stirred at RT. After ca. 10 min all of the K$_2$OsO$_2$(OH)$_4$ was dissolved and the color of the reaction mixture turned to green. Stirring was continued until the green color of the reaction mixture had turned to yellow. 10 ml of acueous Na$_2$SO$_3$ (sat.) were added to reduce excess Chloramine. The aqueous phase was seperated and extracted three times with ca. 30 ml ethyl acetate. The combined organic phases were washed with brine containing 1% of NaOH, dried over MgSO$_4$ (anhydrous) and the solvent was evaporated in vaccu. The residue was purified by flash chromatography (SiO$_2$, hexane/ethyl acetate) to afford the pure crystalline aminohydroxylation product. In cases where regioisomeric products could be formed yields refer to a mixture of the two regioisomeres. Crystallization from ethyl acetate/hexane furnished the enantiomerically pure (>99% ee) N-aryl/alkylsulfonyl protected amino alcohol Catalytic Asymmetric Aminohydroxylation by in situ Generation of Chloramines Different from Chloramine T
(1 mmol Scale, in situ Generation of R—SO$_2$NClNa)

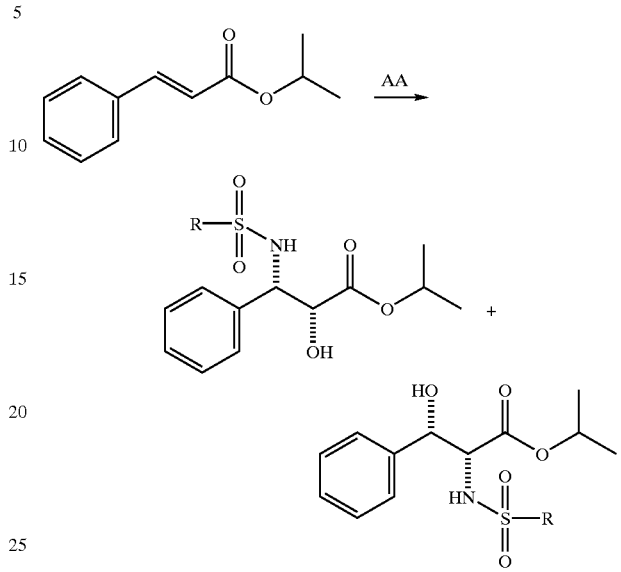

General Procedure:

T-butyl hypochlorite was slowly added to a well stirred solution of the desired sulfonamide (as obtained vida supra; 3.1 mmol, 3.1 eq) and 122 mg (3.05 mmol. 3.05 eq) of NaOH in 7.5 ml of water at room temperature. After 10 more minutes of stirring this solution was added dropwise to absolution of 40 mg (0.05 mmol, 0.05 eq) of (DHQ)$_2$Phal or (DHQD)$_2$Phal in 7.5 ml of MeCN (alternatively, a 1:1 mix of t-BuOH/water, n-propanol/water or 1:1:1 ethanol/n-proanol/water can be used, depending upon optimization conditions). Subsequently 190 mg (1.0 mmol, 1.0 eq) of isopropyl cinnamate (commercially available from Aldrich) and 14.7 mg (0.04 mmol, 0.04 eq) of K$_2$OsO$_2$(OH)$_4$ were added and the reaction mixture stirred at RT. After ca. 10 min all of the K$_2$OsO$_2$(OH)$_4$ was dissolved and the color of the reaction mixture turned to green. Stirring was continued until the green color of the reaction mixture had turned to yellow. 10 ml of aqueous Na$_2$SO$_3$ (sat.) were added to reduce excess Chloramine. The aqueous phase was seperated and extracted three times with ca. 30 ml ethyl acetate. The combined organic phases were washed with brine containing 1% of NaOH, dried over MgSO$_4$ (anhydrous) and the solvent was evaporated in vaccu. The residue was purified by flash chromatography (SiO$_2$, hexane/ethyl acetate) to afford the pure crystalline aminohydoxylation product. In cases where regioisomeric products could be formed yields refer to a mixture of the two regioisomeres. Crystallization from ethyl acetate/hexane furnished the enantiomerically pure (>99% ee) N-aryl/alkylsulfonyl protected amino alcohol.

Preparation of the Chloramine M:(CH$_3$SO$_2$NCl)

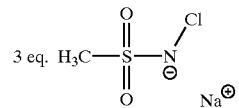

Chloramine M can be synthesized readily from methanesulfonamide (Aldrich chemical company) by addition of the stoichiometric amount of sodium hydroxide and t-butylhypochlorite in water or methanol. This method was adapted from a procedure developed by Campbell et al. *Chem Rev.* 1978, 78, 65, for the preparation of N-chloro-N-sodiocarbamates and proved to be general in the synthesis of N-chloro-N-sodio-aryl- and alkylsulfonamides. Chloramine M can be isolated either as a stable salt or can be prepared in situ, preferable in large scale syntheses.

Synthesis of Chloramine M

To an ice-cold stirred solution of 4.81 g (50 mmol) of methanesulfonamide and 2.0 g (50 mmol) sodium hydroxide in 40 mL of dry methanol is added very slowly 5.63 mL (5.4 g, 50 mmol) t-butylhypochlorite. The solution is stirred for 1 h and dried in vacuo to afford the pure N-chloro, N-sodio-methanesulfonamide in quantitative yield (7.58 g). $CH_3NSO_2NaCl$, MW: 151.54; Elementary analysis: calcd.: C 7.93, H 2.00, N 9.24, Na 15.17, Cl 23.39 found: C 8.03, H 2.08, N 9.24, Na 15.36, Cl 23.12.

For the in situ generation of Chloramine M the preparation can be done in the sufficient amount of water required for the AA reaction by using the same protocol.

General Procedure for Synthesis of Hydroxysufonamides Using Chloramine M ($MeSO_2NClNa$) on a 1 mmol Scale To a well stirred solution of 40 mg of $(DHQD)_2PHAL$ (0.05 mmol, 0.05 eq) in 7.5 ml of n-propanol (alternatively, a 1:1 mix of t-BuOH/water, acetonitrile/water or 1:1:1 ethanol/n-proanol/water can be used, depending upon optimization conditions) was slowly added a solution of 455 mg (3.0 mmol, 3.0 eq) of $MeSO_2NClNa$ in 7.5 ml of water, which resulted in a clear colorless solution. The substrate olefin (all commercially available from Aldrich, 1.0 mmol, 1.0 eq and $K_2OsO_2(OH)_4$ (0.04 mmol, 0.04 eq) were subsequently added. Usually the reaction mixture turned green after some minutes and was stirred until color change to dark blue occured (3–16 h), however colour changes are not generally observed. 10 ml of aqueous $Na_2SO_3$ (sat.) were added to reduce the excess $MeSO_2NClNa$. The aqueous phase was seperated and extracted three times with ca. 30 ml ethyl acetate. The combined organic phases were dried over $MgSO_4$ (anhydrous) and the solvent was evaporated in vacuo.

To determine the exact yield the residue was purified by flash chromatography ($SiO_2$, hexane/ethyl acetate) to afford the pure crystalline aminohydroxylation product. In cases where regioisomeric products can be formed yields refere to a mixture of the two regioisomeres. Crystallization from ethyl acetate/hexane furnished the enantiomerically pure (>99% ee) methane sulfonyl protected amino alcohol.

For preparative purposes work-up and purification can be simplified. As the methanesulfonamide is insoluble in $CH_2Cl_2$ and ether, but good soluble in aqueous solution (even in saturated aqueous NaCl solution) it can be removed extractively. It can also be crystallized out in $CH_2Cl_2$ or $CH_2Cl_2$/hexane mixtures. Alternatively it can be sublimed from the crude material at 80° C. Crystallization from ethyl acetate/hexane could usually furnish the chemically and enantiomerically pure (>99% ee) methane sulfonyl protected amino alcohol.

Asymmetric aminohydroxylation in 1:1 acetonitrile/water

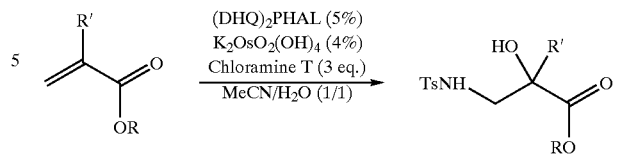

To a stirred solution of $(DHQ)_2$-PHAL (0.11 g, 0.14 mmol, 5 mol %) in 20 mL of acetonitrile and 20 mL of water, in any convenient-sized glass vessel or vial, was added desired acrylate or methacrylates entries 1–10 (all commercially available from Aldrich, 2.8 mmol), Chloramine-T trihydrate (2.42 g, 8.4 mmol, 3 eq) and $K_2OsO_2(OH)_4$ (41.6 mg, 0.112 mmol, 4 mol %). As the reaction proceeded to completion over the course of about one and half hours at room temperature, the color of the solution changed from yellow to pale green, then deep green and finally back to yellow. After addition of aqueous sodium sulfite (1.0 g in 15 mL $H_2O$), the phases were separated, and the aqueous phase extracted with ethyl acetate (3×15 mL). The combined organic extracts were washed with brine, dried over $MgSO_4$ and the solvent concentrated to give the crude product, which also contains the p-toluenesulfonamide by-product produced upon the reduction of the excess Chloramine-T. Purification provides compounds as shown in FIG. 16, entries 1–10 with the indicated yields and conditions. NOTE: Replacement of the 3 eq of Chloramine-T with 1.5 eq of Chloramine-T and 1.5 eq of $Et_4NOAc$ gives comparable results and reduces the amount of p-toluenesulfonamide by-product formed. This can greatly simplify product isolation, especially in cases where the product and the toluenesulfonamide have similar chromatographic mobilities.

Benzyl carbamate (Aldrich) was recrystallyzed from water. t-Butyl carbamate (Arcos) was used without purification. CbzCl (Aldrich) was used without purification. The ligands (DHQ)2PHAL, (DHQD)2PHAL, (DHQ)2AQN, (DHQD)2AQN were prepared according to literature procedures. The K2OsO2(OH)4 (Colonial Metales) was stored dry and dark and used without further purification. Note: The quality of the K2OsO2(OH)4 is crucial for the sucess of the AA reaction. K2OsO2(OH)4 delivered from other companies was not always successful. Stocksolutions of K2OsO2(OH)4 should not be kept for longer than 30 min before use. t-BuOCl was prepared according to literature procedures M. J. Mintz, C. Walling, *Org. Synth. Coll. Vol.* 5 1983, 183–187 and stored dry under nitrogen below 4° C. for not longer than 2 months. Commercially available t-BuOCl, wet t-BuOCl, or t-BuOCl older than 2 months generally gave substandard yields and enantioselectivities. Reagent grade t-BuOH, n-PrOH, p. a. NaOH (Fisher), and standard deionized water were used without purification. The olefins in entry 1, 2, 4, 9, 12, 13. 15, 16 and 17 (in FIG. 12) were purchased from Aldrich. Olfin in entry 14 (FIG. 12) was purchased from Acros. Olfin in entry 10 (FIG. 12) was purchased from Hochst clelanese. Entry 18 (FIG. 12) provided by Merck Pharmacuticals. Entry 6, 7 and 8 were synthesised from corresponding aldehydes by wittig reaction (Aldehydes were purchased from Aldrich). Olefin entry 3 was synthesised from p-hydroxy benzaldehyde in two steps i) benzylation of phenolic hydrohyl group followed by Wittig olefination. Olefine entry 11 (FIG. 12) was synthesised from p-hydroxy benzaldehyde in two steps i) tosylation of phenolic hydroxyl group next wittig olefination of aldehyde function. All these olefines were purified either by destination or crystallization or chromatography.

General Procedure for the Benzyl-carbamate Based AA Described For 4-Benzyloxy-3-methoxy Styrene (Entry 3) 1(S)-N-[(Benzyloxy)carbonyl]-1-[4-(benzyloxy)-3-(methoxy)phenyl]-2-hydroxy Ethylamine (Entry 3) (Ligand=(DHQ)2PHAL) (FIG. 12).

In a 50 mL round bottom flask equipped with a magnetic stirrer, benzyl carbamate (0.940 g, 6.20 mmol) was dissolved in n-PrOH (8 mL). To this stirred solution was added a freshly prepared aqueous solution of NaOH (0.244 g, 6.1 mmol in 15.0 mL water), followed by t-butyl hypochlorite (0.7 mL, 0.662 g, 6.1 mmol). After 5 min. a solution of (DHQ)2PHAL (80 mg, 0.10 mmol, 5 mol %) in n-PrOH (7 mL) was introduced. The reaction mixture should be homogeneous at this point. Then 4-benzyloxy-3-methoxy styrene (0.480 g, 2.0 mmol) was added, followed by K2OsO2(OH)4 (29.4 mg, 0.08 mmol, 4 mol %). The reaction solution was stirred at 25° C. for 1 h. The solution turned from light green to light yellow. After this time the reaction was cooled to 0° C. (ice/water bath) and quenched by the addition of saturated aqueous sodium sulfite (20 mL). The two phases were separated and the aqueous phase was extracted with ethyl acetate (3×15 mL). The combined organic phases were washed with water (2×20 mL), brine (50 mL), dried over anhydrous MgSO4, and concentrated to afford the crude product 25 contaminated with its regioisomer 25B and benzyl carbamate. Flash chromatograpy (SiO2, 5×25 cm, 15–25% EtOAc/hexane gradient elution) afforded pure 3 (0.58 g, 75%, 98% ee) as a colorless solid. M. p. 144–145° C.; $[\alpha]_{D25}$=+38.4o (c=0.5 in 95% EtOH); 1H NMR (400 MHz, CDCl3): δ 7.43–7.28 (m, 10H), 6.84 (d, J=8.2 Hz, 1H), 6.80 (d, J=1.9 Hz, 1H), 6.75 (dd, J=8.2, 1.9 Hz, 1H), 5.4 (d, J=6.2 Hz, 1H), 5.1 (m, 4H), 4.8 (br s, 1H), 3.85 (br s, 5H); 13C NMR (100 MHz, CDCl3): n 156.4, 149.8, 147.8, 137.0, 136.2, 128.6, 128.5, 128.2, 127.9, 127.8, 127.2, 127.1, 118.5, 114.0, 110.5, 71.0, 67.0, 66.4, 56.8, 56.0; HRMS calcd for C24H25NO5 (M+Na)+: 430.1630, found: 430.1640; HPLC chiralcel AD, 15% i-PrOH/hexane, 0.5 mL min-1, 254 nm, 40.5 min(S), 67.2 min(R).

All olefines (entries 1–19 in FIG. 12) were aminohydroxylated according to general procedure as follows:

General Procedure for the t-Butyl-Carbamate Based AA Described for 3,5-Dimethoxy Styrene 1(S)-N-[(t-Butyloxy)carbonyl]-1-[3,5-bis(methoxy) phenyl]-2-hydroxy Ethylamine (21) (Ligand=(DHQ)2PHAL)

A solution of t-butyl carbamate (15.7 g, 134.2 mmol, 3.05 eq) in n-PrOH (172 mL) was sequentially treated with aq. NaOH (5.25 g, 131.0 mmol in 323 mL water) and t-BuOCl (15.1 mL, 14.2 g, 131.2 mmol). After stirring for 5 min the solution was cooled to 0° C. and a solution of (DHQ)2PHAL (2.1 g, 2.6 mmol, 6 mol % dissolved in 172 mL of n-PrOH) was added. The reaction mixture should be homogeneous at this point. Then a solution of 3, 5-dimethoxy styrene (7.2 g, 44.0 mmol dissolved in 300 mL of n-PrOH) was added followed by the solid K2OsO2(OH)4 catalyst (0.647 g, 1.76 mmol, 4 mol %). The reaction mixture was stirred for 1 h at 0° C. The solution turned from light green to light yellow. Two thirds of n-PrOH were removed in vacuo and filtation of resulting slurry gave the product 21 (11.3 g, Total yield 86%, regio selectivity: 3:1) All olefines (entries 19–23 in table 3) were aminohydroxylated according to general procedure as mentioned above.

General Oxidation Procedure for Aminoalcohol to Amino Acid Using TEMPO/NaOCl is Described for 1(S)-N-[(Benzyloxy)carbonyl]-1-[4-(benzyloxy)-3-(methoxy)phenyl]-2-hydroxy Ethylamine 1(S)-N-[(Benzyloxy)carbonyl]-1-[4-(benzyloxy)-3-(methoxy)phenyl]glycine (25):

A solution of amino alcohol 3 (0.41 g, 1.0 mmol) in acetone(5.0 mL) at 0° C. was added to an aqueous 5% NaHCO3 solution (2.5 mL). This hetrogenous miture was treated sequentially with KBr (0.013 g, 0.1 mmol) and TEMPO (0.175 g, 1.2 mmol). Sodium hypochlorite (NaOCl, Aldrich 4–6% 2.5 mL, 1.3 mmol) was added dropwise over 10–15 minutes and the reaction mixture was stirred at 0° C. After 1 h, additional NaOCl (1.3 mL, 0.63 mmol) was added. The reaction solution was stirred for 1 h then H2O (100 mL) was added. The reaction mixture was extrcted with EtOAC (3×100 mL). The Combined Organic layers were washed with H2O (200 mL) and saturated aq NaCl (200 mL), dried (Na2SO4) and concentrated and chomatograpy (Sio2, 3×15 cm, 5–10% CH3OH—CHCl3 gradient elution) afforded acid 25 (0.30 g, 71%, The oxidation reaction is equally working with mixture of regioisomeric alcohols) Same Oxidation procedure was followed for compounds 3, 5, 6 and 7.

General Oxidation Procedure for Aminoalcohol to Amino Acid Using Ruthenium Trichloride-periodic Acid is Described for 1(S)-N-[(Benzyloxy) carbonyl]-1-(phenyl)-2-hydroxy Ethylamine 1(S)-N-[(Benzyloxy)carbonyl]-1-(phenyl)glycine:

In a 100 mL round bottom flask equipped with a magnetic stirrer, N-Cbz phenyl glycinol (1.3 g, 5.0 mmol) was disssolved in CCl4 (100 mL)and acetonitrile (100 mL). To this above solution was added water (15 mL) and periodic acid (4.7 g, 20.1 mmol, 4.1 eq). The reaction mixture was stirred until both phases became clear, then Ruthenium trichloride hydrate (0.025 g, 2.2 mol %). The reaction mixture was stirred at room temperature for 20 min and cooled to 0° C. then methylene cloride (30 mL) was added. The two phases were separated, the aqueous phase was extracted with chloroform (3×20 mL). The combined organic extracts were dried over (Na2SO4) and concentrated to afford the crud product. Flash chromatograpy (SiO2, 5×25 cm, 2–5% CH3OH—CHCl3 gradient elution) afforded pure pure N-Cbz phenyl glycine (1.2 g, 85%). Same Oxidation procedure was followed for compounds 1 and 2. No epimerization was observed during oxidation procedure.

The olefines1–23 were aminohydroxylated according to general procedures vide supra and then (The aminohydroxylated productes1–7) were oxidized to corresponding Amino Acides using the general oxidation procedures (Vida).

Note that The presence of electron withdrawing or electron donating groups in the aromatic ring can also influence the regioselectivity. The data in Table 1 for closely related cases (e.g., entries 3, 10 and 11; FIG. 12) suggests that electron donating substitutents favor isomer A, but the results in entries 13 through 18 indicates that such simple rationales for regioselectivity trends will be of little help fin this system.

Also note that commercially available (S)-(+)-2-phenyl glycinol(Aldrich) and (R)-(–)-2-phenyl glycinol(Acros) were converted to their Cbz-derivatives. The optical rotation and the chiral HPLC behavior were compared with those for the AA products (entry 1, Table 1) obtained from (DHQ)2PHAL or (DHQD)2PHAL, respectively. (S)-N-Cbz phenyl glycinol (commercial): $[\alpha]_{D25}$=+31.0° (c=1 in 95% EtOH); HPLC: chiracel AD, 15% i-PrOH/hexane, 0.7 mL/min, 254 nm, 12.0 min.; Product 1 [(DHQ)2PHAL derived]: $[\alpha]_{D25}$=–29.0° (c=0.5 in 95% EtOH); HPLC: chiracel AD, 15% i-PrOH/hexane, 0.7 mL/min, 254 nm, 12.0 min. (R)-N-Cbz phenyl glycinol (commercial): $[\alpha]_{D25}$=–31.4° (c=1 in 95% EtOH); HPLC: chiracel AD, 15% i-PrOH/hexane, 0.7 mL/min, 254 nm, 16.5 min. (DHQD)2PHAL product of entry 1 (Table 1), $[\alpha]_{D25}$=–28.3° (c=0.5 in 95% EtOH);

HPLC: chiracel AD, 15% i-PrOH/hexane, 0.7 mL/min, 254 nm, 16.5 min. (b) An authentic sample of 1(R)-1-(3-pyridyl)-2-amino ethanol was converted to its Cbz derivative. The the chiral HPLC retention time were compared with the AA product of entry 18 (Table 1) obtained from (DHQD)2PHAL. The Cbz derivative of authentic 1(R)-1-(3-pyridyl)-2-amino ethanol HPLC: chiracel AD, 15% i-PrOH/hexane, 0.7 mL/min, 254 nm, 24.1 min; AA product [(DHQD)2PHAL derived].

Note that 1.1 eq. RCONBrLi and 3.0 reduced osmium and ligand catalyst loading affected neither the regioselectivity nor the enantioselectivity (e.g. the use of 4 mol % ligand and 3 mol % K2OsO2(OH)4 under the standard conditions (e.g. entry 4, FIG. 12). However, reducing the excess equivalents of chloramine salt in carbamate reaction always led to a dramatic decrease of reaction rate. (b) By increasing the ligand concentration at low temperature the ligand acceleration is increased which indirectly reduces the hydrolysis of the osmium-imido complex formed in the catalytic cycle.

Since the two regioisomers are oxidized to two very different compounds (i.e. a carboxlylic acid and a ketone), they need not be separated if the amino acid is the desired product. The crude mixture is oxidaized and the Ketone is removed from the much less soluble N-protected amino acid by trituration or crystallization (if these fail simple filtration chromatography on silica gel is always effective)

What is claimed:

1. A method for converting an olefinic substrate to an asymmetric α-amino aldehyde product, said asymmetric α-amino aldehyde product being selected from a group consisting of deprotected asymmetric α-amino aldehydes and a protected asymmetric α-amino aldehyde intermediate having the protected amino radical, the method comprising the following steps:

Step A: catalytically converting the olefinic substrate by a catalytic asymmetric aminohydroxylation reaction to a protected asymmetric β-aminohydroxide having a protected β-amino radical and a hydroxyl radical, said conversion employing a reaction solution which includes a source of the protected amino radical, an osmium compound as a catalyst, a chiral ligand for enantiomerically directing said catalytic asymmetric aminohydroxylation reaction, and a solvent; then Step B: optionally deprotecting the protected amino radical of the protected asymmetric β-aminohydroxide of said Step A to form a deprotected asymmetric β-aminohydroxide;

Step C: oxidizing the hydroxyl radical on a first intermediate selected from the group consisting of the protected asymmetric β-aminohydroxide of said step A or the deprotected asymmetric β-aminohydroxide of said Step B to form the asymmetric α-amino aldehyde product; and Step D: optionally deprotecting the protected amino radical of the protected asymmetric β-amino aldehyde intermediate of said Step C to form the deprotected asymmetric α-amino aldehyde product.

2. A method for converting an olefinic substrate to an asymmetric α-amino aldehyde product as described in claim 1 wherein:

in said Step A: the source of the protected amino radical is a carbamate and the solvent has an organic component, the olefinic substrate and carbamate being present and soluble at a stoichiometric Molar concentration within the reaction solution, the osmium compound being present and soluble at a catalytic Molar concentration within the reaction solution, and the chiral ligand is present and soluble within the reaction solution at a Molar concentration within a range which is greater or equal to the catalytic Molar concentration of the osmium compound and less than the stoichiometric Molar concentration of the olefinic substrate and carbamate.

3. A method for converting an olefinic substrate to an asymmetric α-amino aldehyde product as decribed in claim 2, wherein:

in said Step A: the Molar concentration of the chiral ligand is within a range approximately equivalent to the catalytic Molar concentration of the osmium compound.

4. A method for converting an olefinic substrate to an asymmetric α-amino aldehyde product as decribed in claim 1 wherein:

in said Step A: the source of the protected amino radical is a carbamate and the solvent has an organic component, the olefinic substrate and carbamate being present and soluble at a stoichiometric Molar concentration within the reaction solution, the osmium compound is present and soluble at a catalytic Molar concentration within the reaction solution, the solvent further including an aqueous component present at 10% or greater on a volume basis; and the chiral ligand is present and soluble within the reaction solution at a Molar concentration with a range which is greater than or equal to the catalytic Molar concentration of the osmium compound and less than stoichiometric Molar concentration of the olefinic substrate and carbamate.

5. A method for converting an olefinic substrate to an asymmetric α-amino aldehyde product as decribed in claim 4, wherein:

in said step A: the Molar concentration of the chiral ligand being within a range approximately equivalent to the catalytic Molar concentration of the osmium compound.

6. A method for converting an olefinic substrate to an asymmetric α-amino aldehyde product as decribed in claim 1 wherein:

in said Step A: the source of the protected amino radical is a sulfonamide.

7. A method for converting an olefinic substrate to an asymmetric α-amino aldehyde product, said asymmetric α-amino aldehyde product being selected from a group consisting of amino aldehydes and protected amino aldehydes having a protected β-amino radical, the method comprising the following steps:

Step A: catalytically converting the olefinic substrate to a protected asymmetric β-aminohydroxide having a protected β-amino radical and a hydroxyl radical by means of catalytic asymmetric oxyamination reaction; then Step B: optionally deprotecting the protected β-amino radical of the protected asymmetric β-aminohydroxide of said Step A to form a deprotected asymmetric β-aminohydroxide;

Step C: oxidizing the hydroxyl radical of a first intermediate selected from the group consisting of the protected asymmetric β-aminohydroxide of said Step A and the deprotected asymmetric β-aminohydroxide of said Step B to form the asymmetric α-amino aldehyde product; and Step D: optionally deprotecting the protected β-amino radical of the protected amino aldehyde to form the amino aldehyde.

8. A method for converting an olefinic substrate to an asymmetric α-amino aldehyde as described in claim 1 wherein the catalytic asymmetric oxyamination reaction of said Step A includes a reaction solution with a source of the protected amino radical, an osmium compound as a catalyst, a chiral ligand, and a solvent.

9. A method for converting an olefinic substrate to an asymmetric α-amino aldedhyde as described in claim 1 wherein the chiral ligand is selected from the group consisting of monovalent cinchona alkaloids, hydroquinine 1,4-phthalazinediyl diether ((DHQ)$_2$PHAL), hydroquinidine 1,4-pthalazinediyl diether ((DHQD)$_2$PHAL), and hydroquinidine-p-chlorobenzoate.

10. A method for converting an olefinic substrate to an asymmetric α-amino aldehyde as described in claim 1 wherein the chiral ligand is selected from the group consisting of hydroquinine 1,4-phthalazinediyl diether ((DHQ)$_2$PHAL) and hydroquinidine 1,4-pthalazinediyl diether ((DHQD)$_2$PHAL).

* * * * *